US012433340B2

(12) United States Patent
Jackson et al.

(10) Patent No.: US 12,433,340 B2
(45) **Date of Patent: *Oct. 7, 2025**

(54) AEROSOL DELIVERY DEVICE CONSUMABLE UNIT

(71) Applicant: R. J. Reynolds Tobacco Company, Winston Salem, NC (US)

(72) Inventors: Cortney Rasheen Jackson, Colfax, NC (US); Thaddeus Jackson, Summerfield, NC (US); Keri Meggan Cox, Greensboro, NC (US); Karen H. Cleckley, Kernersville, NC (US); Billy T. Conner, Clemmons, NC (US)

(73) Assignee: R. J. REYNOLDS TOBACCO COMPANY, Winston-Salem, NC (US)

( * ) Notice: Subject to any disclaimer, the term of this patent is extended or adjusted under 35 U.S.C. 154(b) by 544 days.

This patent is subject to a terminal disclaimer.

(21) Appl. No.: 17/221,311

(22) Filed: Apr. 2, 2021

(65) Prior Publication Data

US 2022/0312846 A1 Oct. 6, 2022

(51) Int. Cl.

*A24F 40/465* (2020.01)
*A24D 1/22* (2020.01)
(Continued)

(52) U.S. Cl.

CPC .............. *A24F 40/465* (2020.01); *A24D 1/22* (2020.01); *H05B 6/065* (2013.01); *H05B 6/105* (2013.01); *A61M 15/06* (2013.01)

(58) Field of Classification Search

None
See application file for complete search history.

(56) References Cited

U.S. PATENT DOCUMENTS 1,464,300 A 8/1923 Taff
1,505,655 A 8/1924 Marek
(Continued)

FOREIGN PATENT DOCUMENTS

JP 2002034543 2/2002
WO WO1995034226 12/1995
(Continued)

OTHER PUBLICATIONS

"Pouch." Merriam-Webster.com Dictionary, Merriam-Webster (2024), https://www.merriam-webster.com/dictionary/pouch. Accessed Feb. 9, 2024. (Year: 2024).*
(Continued)

*Primary Examiner* — Philip Y Louie
*Assistant Examiner* — Jeffrey A. Buckman
(74) *Attorney, Agent, or Firm* — Womble Bond Dickinson (US) LLP

(57) ABSTRACT

The present disclosure is directed to an aerosol delivery device and a consumable unit for use with a holder of an aerosol delivery device. In one example implementation, the consumable unit comprises an ignitable heat source and a substrate material having an aerosol precursor composition configured to form an aerosol upon application of heat thereto. The heat source of the consumable unit is contained within a susceptor pouch, and the susceptor pouch is configured to be heated by an inductive heating assembly to ignite the heat source. In some implementations, the susceptor pouch comprises the consumable unit. In other implementations, the substrate material is contained within a substrate container.

20 Claims, 8 Drawing Sheets

(51) Int. Cl.

*H05B 6/06* (2006.01)
*H05B 6/10* (2006.01)
*A61M 15/06* (2006.01)

(56) References Cited

U.S. PATENT DOCUMENTS

| | | | | |
|---|---|---|---|---|
| 1,541,891 | A | 6/1925 | Becker | |
| 1,607,132 | A | 11/1926 | Shichigoro | |
| 1,613,545 | A | 1/1927 | Teigen | |
| 1,941,531 | A | 1/1934 | Blankenship | |
| 2,008,433 | A | 7/1935 | Ashour | |
| 2,373,629 | A | 4/1945 | Daugherty | |
| 2,455,492 | A | 12/1948 | Jackson | |
| 2,502,831 | A | 4/1950 | Henry | |
| 2,541,837 | A | 2/1951 | Schroff | |
| 2,701,571 | A | 2/1955 | Dittrich | |
| 2,711,176 | A | 6/1955 | Vakilian | |
| 2,779,340 | A | 1/1957 | Lee | |
| 2,953,136 | A | 9/1960 | Dahly | |
| 3,155,099 | A | 11/1964 | Minchin | |
| 3,181,538 | A | 5/1965 | Piliego | |
| 3,685,520 | A | 8/1972 | Chernack | |
| 3,986,516 | A * | 10/1976 | Brooks | A24F 5/06 131/185 |
| 4,708,151 | A | 11/1987 | Shelar | |
| 4,714,082 | A | 12/1987 | Banerjee et al. | |
| 4,966,171 | A | 10/1990 | Serrano et al. | |
| 4,991,606 | A | 2/1991 | Serrano et al. | |
| 5,040,552 | A | 8/1991 | Schleich et al. | |
| 5,060,676 | A | 10/1991 | Hearn et al. | |
| 5,076,296 | A | 12/1991 | Nystrom et al. | |
| 5,159,940 | A | 11/1992 | Hayward et al. | |
| 5,178,165 | A | 1/1993 | DeFelice | |
| 5,240,012 | A | 8/1993 | Ehrman et al. | |
| 5,592,955 | A | 1/1997 | Keritsis | |
| 5,595,577 | A | 1/1997 | Bensalem et al. | |
| 5,692,525 | A | 12/1997 | Counts et al. | |
| 5,845,649 | A | 12/1998 | Saito et al. | |
| 6,006,757 | A | 12/1999 | Lichtenberg | |
| 6,053,176 | A | 4/2000 | Adams et al. | |
| 6,164,287 | A | 12/2000 | White | |
| 6,311,694 | B1 | 11/2001 | Nichols et al. | |
| 6,345,625 | B1 | 2/2002 | Chew | |
| 6,371,127 | B1 | 4/2002 | Snaidr et al. | |
| 6,431,177 | B1 | 8/2002 | Sieggen et al. | |
| 6,532,965 | B1 | 3/2003 | Abhulimen et al. | |
| 6,615,843 | B2 | 9/2003 | Pera | |
| 6,748,955 | B2 | 6/2004 | Snaidr et al. | |
| 7,080,649 | B2 | 7/2006 | Hcu | |
| 7,503,330 | B2 | 3/2009 | Borschke et al. | |
| 7,600,517 | B1 | 10/2009 | Holzrichter | |
| 7,624,739 | B2 | 12/2009 | Snaidr et al. | |
| 8,061,361 | B2 | 11/2011 | Maeder et al. | |
| 8,151,803 | B2 | 4/2012 | Inagaki | |
| 8,302,611 | B2 | 11/2012 | Rowley | |
| 8,528,567 | B2 | 9/2013 | Hajaligol | |
| 8,616,217 | B2 | 12/2013 | Tsurizumi et al. | |
| 8,776,803 | B2 | 7/2014 | Tarora et al. | |
| 8,863,754 | B2 | 10/2014 | Renaud et al. | |
| 8,915,255 | B2 | 12/2014 | Poget et al. | |
| 9,078,473 | B2 | 7/2015 | Worm et al. | |
| 9,149,072 | B2 | 10/2015 | Conner et al. | |
| 9,220,301 | B2 | 12/2015 | Banerjee et al. | |
| 9,282,769 | B2 | 3/2016 | Mishra et al. | |
| 9,301,546 | B2 | 4/2016 | Thomas et al. | |
| 9,332,784 | B2 | 5/2016 | Banerjee et al. | |
| 9,439,453 | B2 | 9/2016 | Conner et al. | |
| 9,532,591 | B2 | 1/2017 | Mironov | |
| 9,549,572 | B2 | 1/2017 | Dincer et al. | |
| 9,609,893 | B2 | 4/2017 | Novak, III et al. | |
| 9,629,393 | B2 | 4/2017 | Stolz et al. | |
| 9,693,587 | B2 | 7/2017 | Plojoux | |
| 9,717,273 | B2 | 8/2017 | Poget et al. | |
| 9,730,468 | B2 | 8/2017 | Poget et al. | |
| 9,801,412 | B2 | 10/2017 | Grant | |
| 9,894,930 | B2 | 2/2018 | Bonici et al. | |
| 9,918,494 | B2 | 3/2018 | Mironov et al. | |
| 9,930,915 | B2 | 4/2018 | Worm et al. | |
| 9,943,114 | B2 | 4/2018 | Batista | |
| 9,961,939 | B2 | 5/2018 | Reevell | |
| 10,022,014 | B2 | 7/2018 | Mateos Martin et al. | |
| 10,034,493 | B2 | 7/2018 | Akiyama et al. | |
| 10,062,015 | B2 | 8/2018 | Besehanic | |
| 10,064,428 | B2 | 9/2018 | Swepston et al. | |
| 10,064,478 | B2 | 9/2018 | Brooks | |
| 10,082,015 | B2 | 9/2018 | Williams et al. | |
| 10,102,013 | B2 | 10/2018 | Preston et al. | |
| 10,111,463 | B2 | 10/2018 | Batista | |
| 10,132,009 | B2 | 11/2018 | Chou et al. | |
| 10,159,277 | B2 | 12/2018 | Bonnely | |
| 10,212,014 | B2 | 2/2019 | Qu et al. | |
| 10,212,968 | B2 | 2/2019 | Mironov et al. | |
| 10,222,015 | B2 | 3/2019 | Chien | |
| 10,262,017 | B2 | 4/2019 | Wolge | |
| 10,291,991 | B2 | 5/2019 | Shan et al. | |
| 10,301,990 | B2 | 5/2019 | De Smet et al. | |
| 10,302,018 | B2 | 5/2019 | Venter | |
| 10,312,017 | B2 | 6/2019 | Huang et al. | |
| 10,398,168 | B2 | 9/2019 | Maiwald et al. | |
| 10,470,491 | B2 | 11/2019 | Sutton et al. | |
| 10,492,526 | B2 | 12/2019 | Sampson et al. | |
| 10,524,503 | B2 | 1/2020 | Florack et al. | |
| 10,827,780 | B2 | 11/2020 | Swepston et al. | |
| 2007/0283972 | A1 * | 12/2007 | Monsees | A61M 15/06 131/273 |
| 2008/0047570 | A1 | 2/2008 | Plank | |
| 2009/0065011 | A1 | 3/2009 | Maeder et al. | |
| 2011/0083674 | A1 | 4/2011 | Karpinsky | |
| 2013/0133675 | A1 | 5/2013 | Shinozaki et al. | |
| 2013/0167850 | A1 | 7/2013 | Al-Aawar | |
| 2013/0228190 | A1 | 9/2013 | Weiss et al. | |
| 2014/0048085 | A1 | 2/2014 | Cox | |
| 2015/0034100 | A1 | 2/2015 | Park et al. | |
| 2015/0040924 | A1 | 2/2015 | Mironov et al. | |
| 2015/0296882 | A1 | 10/2015 | Mironov et al. | |
| 2015/0342254 | A1 | 12/2015 | Mironov et al. | |
| 2016/0007648 | A1 | 1/2016 | Sutton et al. | |
| 2016/0007649 | A1 | 1/2016 | Sampson et al. | |
| 2016/0120216 | A1 | 5/2016 | Mironov et al. | |
| 2016/0135495 | A1 | 5/2016 | Poget et al. | |
| 2016/0174609 | A1 | 6/2016 | Mironov | |
| 2016/0192704 | A1 | 7/2016 | Bonnely | |
| 2016/0316816 | A1 | 11/2016 | Lavanchy et al. | |
| 2016/0360785 | A1 | 12/2016 | Bless et al. | |
| 2017/0000189 | A1 | 1/2017 | Mironov et al. | |
| 2017/0055577 | A1 | 3/2017 | Batista | |
| 2017/0055578 | A1 | 3/2017 | Oda et al. | |
| 2017/0119048 | A1 * | 5/2017 | Kaufman | H05B 6/105 |
| 2017/0164654 | A1 | 6/2017 | Ademe | |
| 2017/0196261 | A1 | 7/2017 | Borges De Couraca et al. | |
| 2017/0303585 | A1 | 10/2017 | Florack et al. | |
| 2017/0318859 | A1 | 11/2017 | Batista | |
| 2018/0000165 | A1 | 1/2018 | Liu | |
| 2018/0014571 | A1 | 1/2018 | Nakano | |
| 2018/0070640 | A1 | 3/2018 | Bessant et al. | |
| 2018/0116280 | A1 | 5/2018 | Maiwald et al. | |
| 2018/0192707 | A1 | 7/2018 | Worm et al. | |
| 2018/0279681 | A1 * | 10/2018 | Rojo-Calderon | A24D 1/20 |
| 2018/0317560 | A1 | 11/2018 | Shinozaki et al. | |
| 2018/0325167 | A1 | 11/2018 | Grant | |
| 2018/0368468 | A1 | 12/2018 | Mishra et al. | |
| 2019/0000135 | A1 | 1/2019 | Lavanant et al. | |
| 2019/0000141 | A1 | 1/2019 | Rojo-Calderon et al. | |
| 2019/0000142 | A1 | 1/2019 | Lavanchy et al. | |
| 2019/0014818 | A1 | 1/2019 | Saygili | |
| 2019/0014820 | A1 | 1/2019 | Malgat | |
| 2019/0014821 | A1 | 1/2019 | Batista et al. | |
| 2019/0053535 | A1 * | 2/2019 | Apetrei Birza | A24B 15/167 |
| 2019/0059449 | A1 | 2/2019 | Akiyama et al. | |
| 2019/0059450 | A1 | 2/2019 | Akiyama et al. | |
| 2019/0075848 | A1 | 3/2019 | Worm et al. | |
| 2019/0124972 | A1 | 5/2019 | Nakano | |
| 2019/0124973 | A1 | 5/2019 | Nakano et al. | |
| 2019/0133176 | A1 | 5/2019 | Nakano et al. | |

(56) References Cited

U.S. PATENT DOCUMENTS

| | | | | |
|---|---|---|---|---|
| 2019/0150505 | A1 | 5/2019 | Ceppi et al. | |
| 2019/0274358 | A1 | 9/2019 | Reevell | |
| 2020/0015519 | A1 | 1/2020 | Conner et al. | |
| 2020/0060333 | A1 | 2/2020 | Sutton et al. | |
| 2020/0146349 | A1 | 5/2020 | Phillips et al. | |
| 2020/0237018 | A1* | 7/2020 | Sur | H05B 6/108 |
| 2020/0268044 | A1 | 8/2020 | Wilson | |
| 2021/0015172 | A1 | 1/2021 | Conner et al. | |
| 2021/0015174 | A1 | 1/2021 | Cox et al. | |
| 2021/0015175 | A1 | 1/2021 | Jackson et al. | |
| 2021/0037880 | A1* | 2/2021 | Rogan | A24F 42/10 |
| 2021/0205552 | A1* | 7/2021 | Conner | A24D 1/20 |
| 2021/0315255 | A1* | 10/2021 | Mua | A24B 15/14 |
| 2022/0322734 | A1* | 10/2022 | Batista | A24D 1/20 |
| 2022/0386697 | A1* | 12/2022 | Batista | H05B 6/105 |

FOREIGN PATENT DOCUMENTS

| | | | |
|---|---|---|---|
| WO | WO1998054989 | | 12/1998 |
| WO | WO2009022232 | | 2/2009 |
| WO | WO2013072336 | | 5/2013 |
| WO | WO2013083963 | | 6/2013 |
| WO | WO2013149810 | | 10/2013 |
| WO | WO2013189836 | | 12/2013 |
| WO | WO2014037270 | | 3/2014 |
| WO | WO2014180893 | | 11/2014 |
| WO | WO2015097005 | | 7/2015 |
| WO | WO2015128384 | | 9/2015 |
| WO | WO2015151158 | | 10/2015 |
| WO | WO2015184744 | | 12/2015 |
| WO | WO2015197850 | | 12/2015 |
| WO | WO2017042297 | | 3/2017 |
| WO | WO2017108912 | | 6/2017 |
| WO | WO2017114760 | | 7/2017 |
| WO | WO2017115181 | | 7/2017 |
| WO | WO2017115182 | | 7/2017 |
| WO | WO2017115183 | | 7/2017 |
| WO | WO2017115184 | | 7/2017 |
| WO | WO2017115185 | | 7/2017 |
| WO | WO2017115188 | | 7/2017 |
| WO | WO2017115196 | | 7/2017 |
| WO | WO2017207442 | | 12/2017 |
| WO | WO2017212284 | | 12/2017 |
| WO | WO2018170800 | | 9/2018 |
| WO | WO2018201655 | | 11/2018 |
| WO | WO2019010680 | | 1/2019 |
| WO | 2019/207027 | A1 | 10/2019 |
| WO | 2020/070844 | A1 | 4/2020 |
| WO | 2020/127122 | A1 | 6/2020 |
| WO | WO2020216762 | | 10/2020 |

OTHER PUBLICATIONS

"Pouch." Cambridge Advanced Learner's Dictionary & Thesaurus, Cambridge University Press (2024), https://dictionary.cambridge.org/us/dictionary/english/pouch. Accessed Feb. 9, 2024. (Year: 2024).*

"Pouch." Vocabulary.com Dictionary, Vocabulary.com (2024), https://www.vocabulary.com/dictionary/pouch. Accessed Feb. 9, 202 (Year: 2024).*

International Search Report from the corresponding International patent application No. PCT/IB2022/053073, mailed Jul. 1, 2022. 4 pages.

* cited by examiner

AEROSOL DELIVERY DEVICE CONSUMABLE UNIT

FIELD OF THE DISCLOSURE

The present disclosure relates to aerosol delivery devices and systems, such as smoking articles; and more particularly, to aerosol delivery devices and systems that utilize heat sources, such as combustible carbon-based ignition sources, for the production of aerosol (e.g., smoking articles for purposes of yielding components of tobacco, tobacco extracts, nicotine, synthetic nicotine, non-nicotine flavoring, and other materials in an inhalable form, commonly referred to as heat-not-burn systems or electronic cigarettes). Components of such articles may be made or derived from tobacco, or those articles may be characterized as otherwise incorporating tobacco for human consumption, and which may be capable of vaporizing components of tobacco and/or other tobacco related materials to form an inhalable aerosol for human consumption.

BACKGROUND

Many smoking articles have been proposed through the years as improvements upon, or alternatives to, smoking products based upon combusting tobacco. Example alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference in its entirety.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. App. Pub. No. 2009/0095311 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and WO 2010/091593 to Hon, which are incorporated herein by reference.

Various manners and methods for assembling smoking articles that possess a plurality of sequentially arranged segmented components have been proposed. See, for example, the various types of assembly techniques and methodologies set forth in U.S. Pat. No. 5,469,871 to Barnes et al. and U.S. Pat. No. 7,647,932 to Crooks et al.; and U.S. Pat. App. Pub. Nos. 2010/0186757 to Crooks et al.; 2012/0042885 to Stone et al., and 2012/00673620 to Conner et al.; each of which is incorporated by reference herein in its entirety.

Certain types of cigarettes that employ carbonaceous fuel elements have been commercially marketed under the brand names "Premier," "Eclipse" and "Revo" by R. J. Reynolds Tobacco Company. See, for example, those types of cigarettes described in Chemical and Biological Studies on New Cigarette Prototypes that Heat Instead of Burn Tobacco, R. J. Reynolds Tobacco Company Monograph (1988) and Inhalation Toxicology, 12:5, p. 1-58 (2000). Additionally, a similar type of cigarette has been marketed in Japan by Japan Tobacco Inc. under the brand name "Steam Hot One."

In some instances, some smoking articles, particularly those that employ a traditional paper wrapping material, are also prone to scorching of the paper wrapping material overlying an ignitable fuel source, due to the high temperature attained by the fuel source in proximity to the paper wrapping material. This can reduce enjoyment of the smoking experience for some consumers and can mask or undesirably alter the flavors delivered to the consumer by the aerosol delivery components of the smoking articles. In further instances, traditional types of smoking articles can produce relatively significant levels of gasses, such as carbon monoxide and/or carbon dioxide, during use (e.g., as products of carbon combustion). In still further instances, traditional types of smoking articles may suffer from poor performance with respect to aerosolizing the aerosol forming component(s).

As such, it would be desirable to provide smoking articles that address one or more of the technical problems sometimes associated with traditional types of smoking articles. In particular, it would be desirable to provide a smoking article that is easy to use and that provides reusable and/or replaceable components.

BRIEF SUMMARY

In various implementations, the present disclosure relates to aerosol delivery devices and removable and replaceable consumable units. The present disclosure includes, without limitation, the following example implementations.

Example Implementation 1: An aerosol delivery device comprising a consumable unit comprising an ignitable heat source and a substrate material having an aerosol precursor composition configured to form an aerosol upon application of heat thereto, and a holder comprising a main body defining a proximal end and a distal end, the main body further defining a receiving chamber configured to receive the consumable unit and an aerosol passageway that extends through at least a portion of the main body, and an inductive heating assembly, wherein the heat source of the consumable unit is contained within a susceptor pouch, and wherein the inductive heating assembly is configured to heat the susceptor pouch to ignite the ignitable heat source.

Example Implementation 2: The aerosol delivery device of Example Implementation 1, or any combination of preceding example implementations, wherein the substrate material is contained within a substrate container, and wherein at least a portion of the substrate pouch is in contact with the substrate material.

Example Implementation 3: The aerosol delivery device of any one of Example Implementations 1-2, or any combination of preceding example implementations, wherein the substrate container comprises a substrate tube.

Example Implementation 4: The aerosol delivery device of any one of Example Implementations 1-3, or any combination of preceding example implementations, wherein at least a portion of the substrate tube is constructed of a paper material.

Example Implementation 5: The aerosol delivery device of any one of Example Implementations 1-4, or any combination of preceding example implementations, wherein the substrate material is also contained within the susceptor pouch such that the susceptor pouch comprises the consumable unit.

Example Implementation 6: The aerosol delivery device of any one of Example Implementations 1-5, or any combination of preceding example implementations, wherein the inductive heating assembly includes a resonant transmitter comprising an inductor coil located proximate at least a portion of the receiving chamber.

Example Implementation 7: The aerosol delivery device of any one of Example Implementations 1-6, or any combination of preceding example implementations, wherein the susceptor pouch comprises a mesh structure.

Example Implementation 8: The aerosol delivery device of any one of Example Implementations 1-7, or any combination of preceding example implementations, wherein the susceptor pouch is made of a susceptor material.

Example Implementation 9: The aerosol delivery device of any one of Example Implementations 1-8, or any combination of preceding example implementations, wherein the inductive heating assembly comprises a first portion configured to heat the susceptor pouch, and a second portion configured to heat the portion of the substrate material.

Example Implementation 10: The aerosol delivery device of any one of Example Implementations 1-9, or any combination of preceding example implementations, wherein the first and second portions are independently controllable.

Example Implementation 11: A consumable unit for use with a holder of an aerosol delivery device, the consumable unit comprising an ignitable heat source, and a substrate material having an aerosol precursor composition configured to form an aerosol upon application of heat thereto, wherein the heat source of the consumable unit is contained within a susceptor pouch, and wherein the susceptor pouch is configured to be heated by an inductive heating assembly to ignite the heat source.

Example Implementation 12: The consumable unit of Example Implementation 11, or any combination of preceding example implementations, wherein the substrate material is contained within a substrate container, and wherein at least a portion of the substrate pouch is in contact with the substrate material.

Example Implementation 13: The consumable unit of any one of Example Implementations 11-12, or any combination of preceding example implementations, wherein the substrate container comprises a substrate tube.

Example Implementation 14: The consumable unit of any one of Example Implementations 11-13, or any combination of preceding example implementations, wherein at least a portion of the substrate tube is constructed of a paper material.

Example Implementation 15: The consumable unit of any one of Example Implementations 11-14, or any combination of preceding example implementations, wherein the substrate material is also contained within the susceptor pouch such that the susceptor pouch comprises the consumable.

Example Implementation 16: The consumable unit of any one of Example Implementations 11-15, or any combination of preceding example implementations, wherein the inductive heating assembly includes a resonant transmitter comprising an inductor coil located proximate at least a portion of the receiving chamber.

Example Implementation 17: The consumable unit of any one of Example Implementations 11-16, or any combination of preceding example implementations, wherein the susceptor pouch comprises a mesh structure.

Example Implementation 18: The consumable unit of any one of Example Implementations 11-17, or any combination of preceding example implementations, wherein the susceptor pouch is made of a susceptor material.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWINGS

Figure 1:
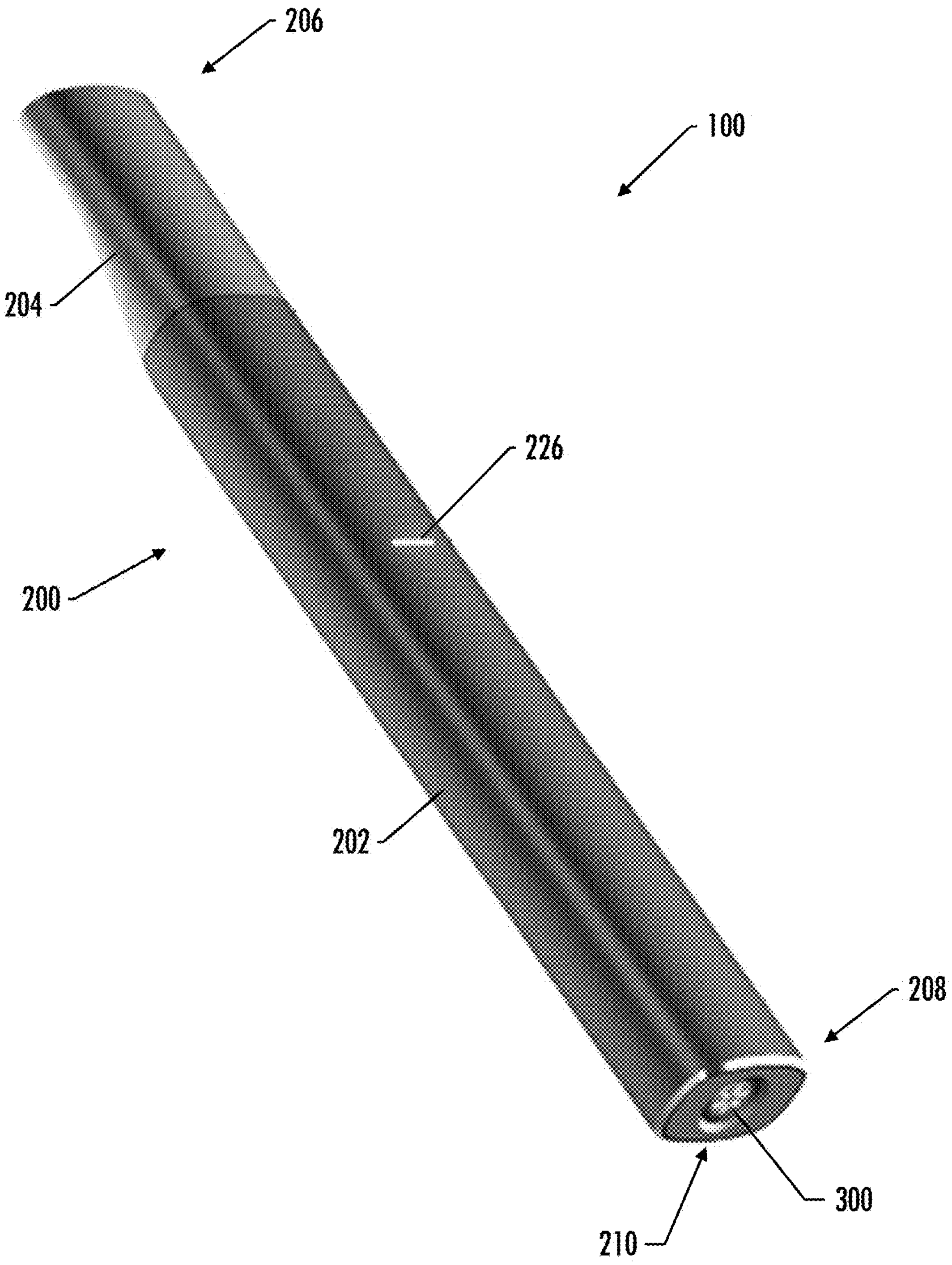
Figure 2:
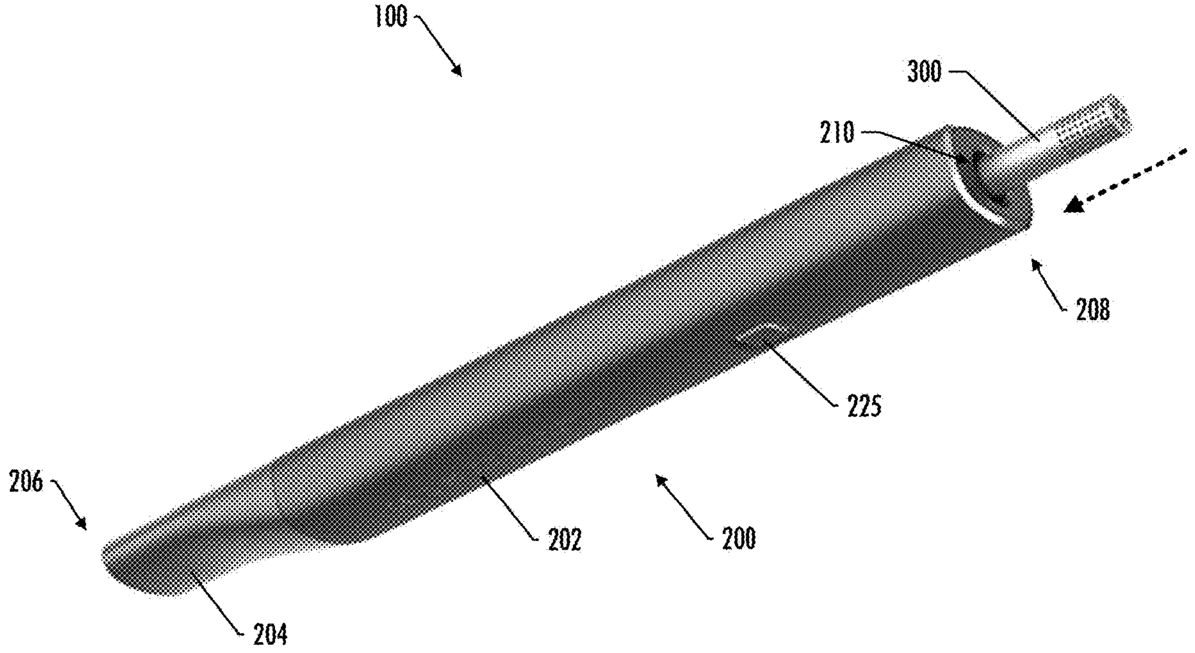
Figure 3:
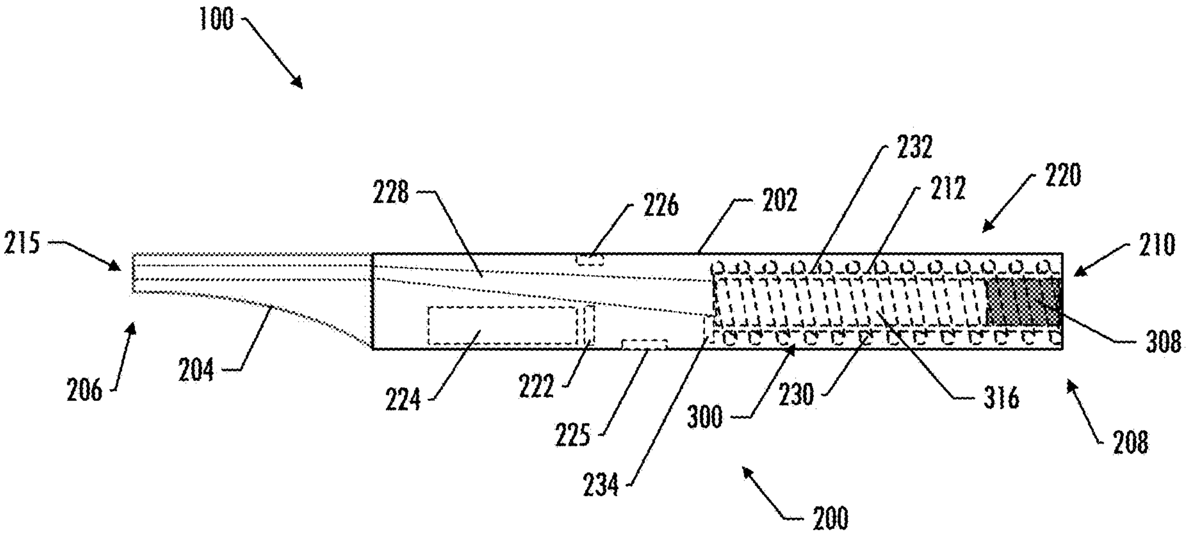
Figure 4:
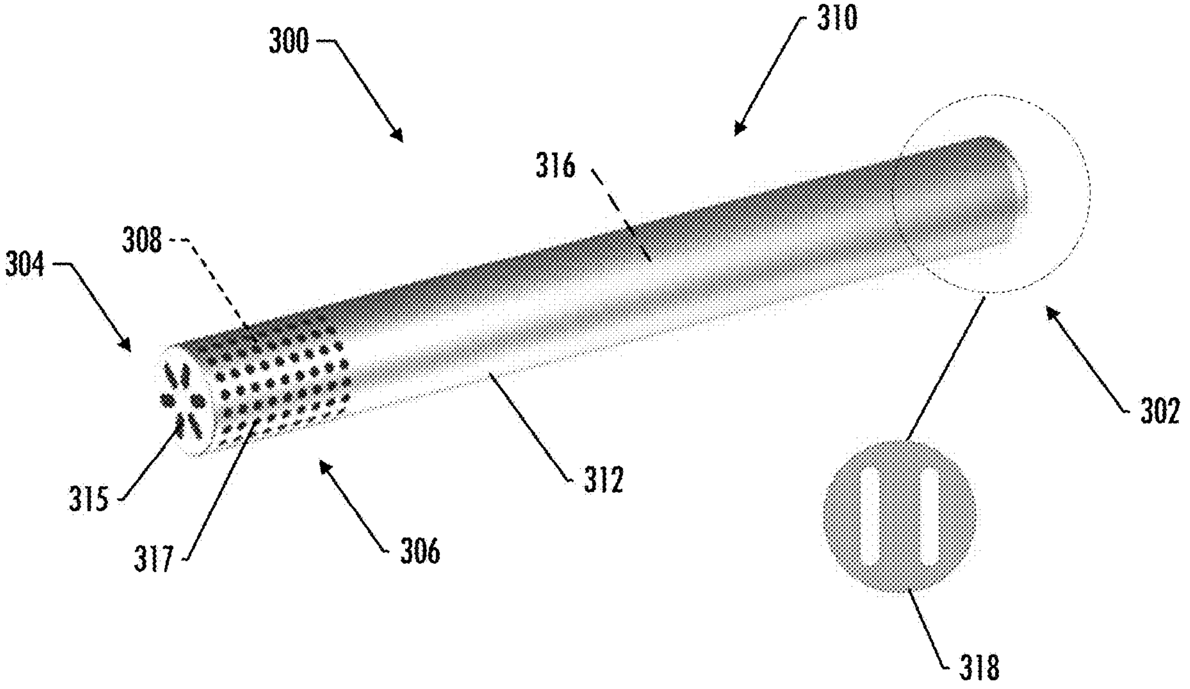
Figure 5:
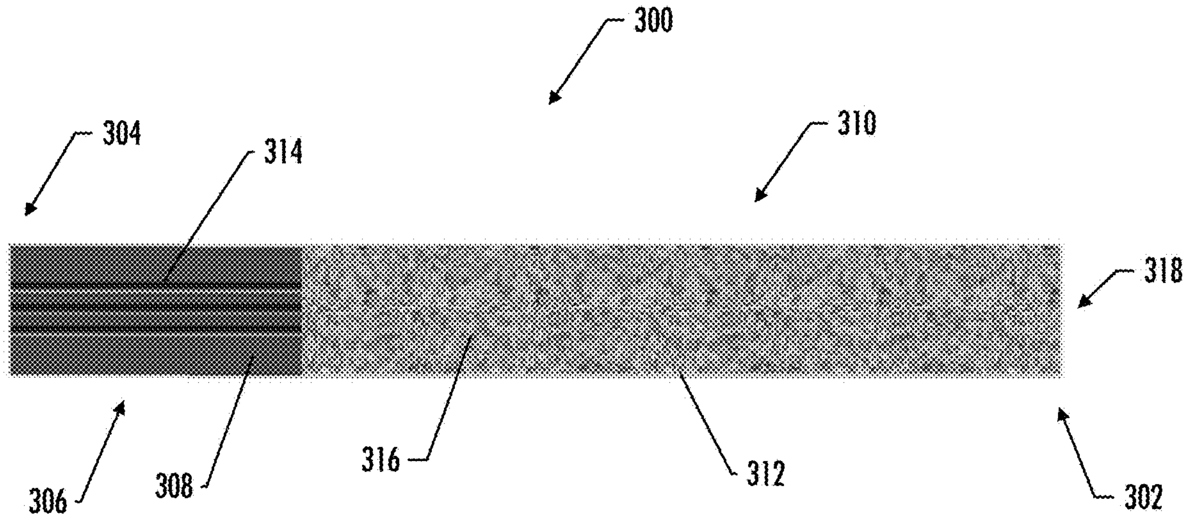
Figure 6:
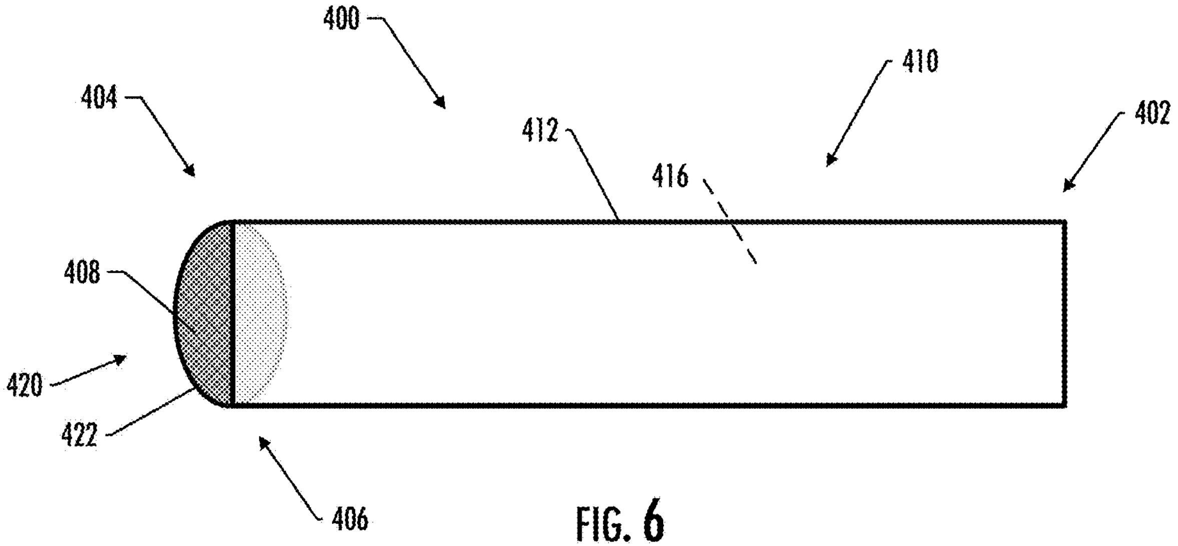
Figure 7:
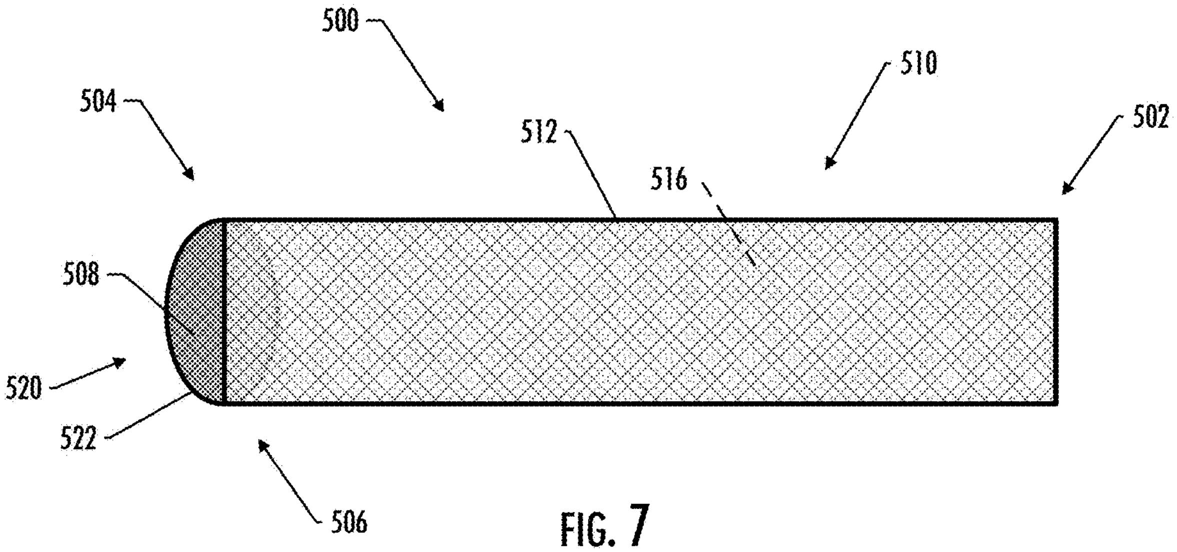
Figure 8:
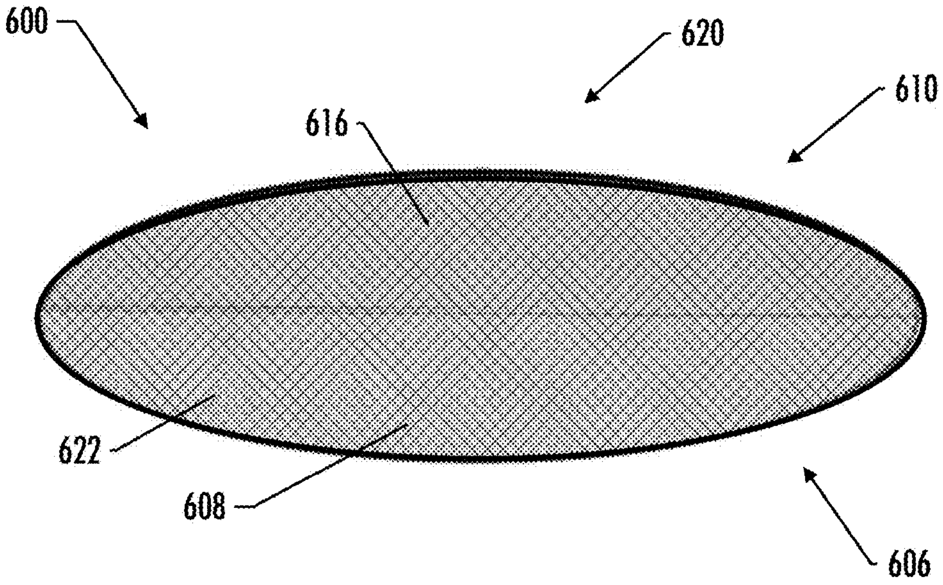
Figure 9:
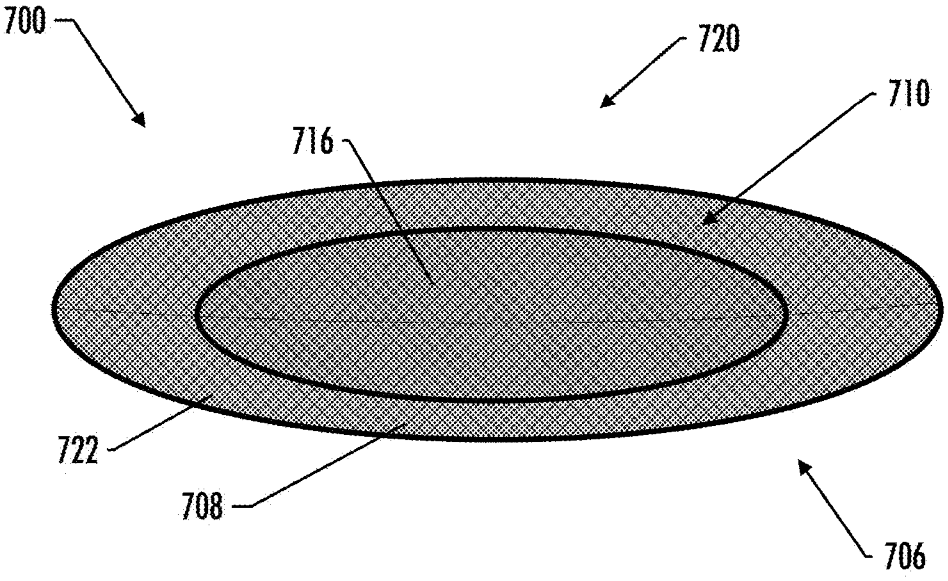
Figure 10:
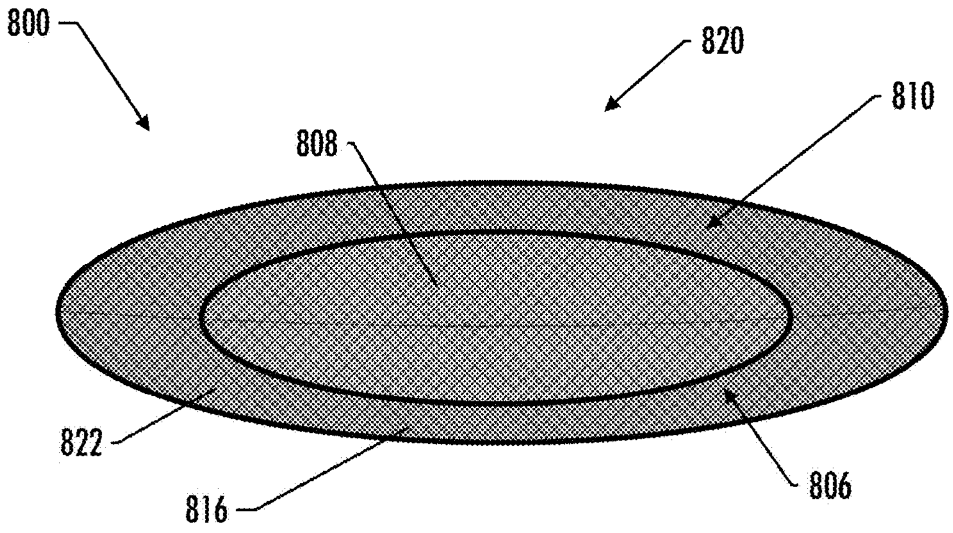

Having thus described the disclosure in the foregoing general terms, reference will now be made to the accompanying drawings, which are not necessarily drawn to scale, and wherein:

FIG. 1 illustrates perspective view of an aerosol delivery device comprising a holder and a removable consumable unit, according to one implementation of the present disclosure;

FIG. 2 illustrates a reverse perspective view of an aerosol delivery device comprising a holder and a removable consumable unit, according to one implementation of the present disclosure;

FIG. 3 illustrates a schematic view of an aerosol delivery device comprising a holder and a removable consumable unit, according to one implementation of the present disclosure;

FIG. 4 illustrates a perspective view of a removable consumable unit, according to one implementation of the present disclosure;

FIG. 5 illustrates a longitudinal cross-section view of a removable consumable unit, according to one implementation of the present disclosure;

FIG. 6 illustrates a schematic view of a removable consumable unit, according to one implementation of the present disclosure;

FIG. 7 illustrates a schematic view of a removable consumable unit, according to one implementation of the present disclosure;

FIG. 8 illustrates a schematic cross-section view of a removable consumable unit, according to one implementation of the present disclosure;

FIG. 9 illustrates a schematic cross-section view of a removable consumable unit, according to one implementation of the present disclosure; and FIG. 10 illustrates a schematic cross-section view of a removable consumable unit, according to one implementation of the present disclosure.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure is embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure provides descriptions of articles (and the assembly and/or manufacture thereof) in which a material is heated (preferably without combusting the material to any significant degree) to form an aerosol and/or an inhalable substance; such articles most preferably being sufficiently compact to be considered "hand-held" devices. In some aspects, the articles are characterized as smoking articles. As used herein, the term "smoking article" is intended to mean an article and/or device that provides many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article and/or device. As used herein, the term "smoking article" does not necessarily mean that, in operation, the article or device produces smoke in the sense of an aerosol resulting from by-products of combustion or pyrolysis of tobacco, but rather, that the article or device yields vapors (including vapors within aerosols that are considered to be visible aerosols that might be considered to be described as smoke-like) resulting from volatilization or vaporization of certain components, elements, and/or the like of the article and/or device. In some aspects, articles or devices characterized as smoking articles incorporate tobacco and/or components derived from tobacco.

As noted, aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol delivery device in accordance with some example implementations of the present disclosure can hold and use that device much like a smoker employs a traditional type of smoking article, draw on one end of that piece for inhalation of aerosol produced by that piece, take or draw puffs at selected intervals of time, and the like.

Articles or devices of the present disclosure are also characterized as being vapor-producing articles, aerosol delivery articles, or medicament delivery articles. Thus, such articles or devices are adaptable so as to provide one or more substances in an inhalable form or state. For example, inhalable substances are substantially in the form of a vapor (e.g., a substance that is in the gas phase at a temperature lower than its critical point). Alternatively, inhalable substances are in the form of an aerosol (e.g., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like. In some implementations, the terms "vapor" and "aerosol" may be interchangeable. Thus, for simplicity, the terms "vapor" and "aerosol" as used to describe the disclosure are understood to be interchangeable unless stated otherwise.

In use, smoking articles of the present disclosure are subjected to many of the physical actions of an individual in using a traditional type of smoking article (e.g., a cigarette, cigar, or pipe that is employed by lighting with a flame and used by inhaling tobacco that is subsequently burned and/or combusted). For example, the user of a smoking article of the present disclosure holds that article much like a traditional type of smoking article, draws on one end of that article for inhalation of an aerosol produced by that article, and takes puffs at selected intervals of time.

While the systems are generally described herein in terms of implementations associated with smoking articles such as so-called "tobacco heating products," it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Aerosol delivery devices of the present disclosure generally include a number of components provided within an outer body or shell, which may be referred to as a housing. The overall design of the outer body or shell can vary, and the format or configuration of the outer body that can define the overall size and shape of the aerosol delivery device can vary. In some example implementations, an elongated body resembling the shape of a cigarette or cigar can be formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In another example, an aerosol delivery device may be substantially rectangular or have a substantially rectangular cuboid shape. In one example, all of the components of the aerosol delivery device are contained within one housing.

Alternatively, an aerosol delivery device can comprise two or more housings that are joined and are separable. For example, an aerosol delivery device can possess one portion comprising a housing containing one or more reusable components (e.g., an accumulator such as a rechargeable battery and/or rechargeable supercapacitor, and various electronics for controlling the operation of that article), and removably coupleable thereto, another second portion (e.g., a mouthpiece) and/or a disposable component (e.g., a disposable flavor-containing consumable unit containing aerosol precursor material, flavorant, etc.). More specific formats, configurations and arrangements of components within the single housing type of unit or within a multi-piece separable housing type of unit will be evident in light of the further disclosure provided herein. Additionally, various aerosol delivery device designs and component arrangements can be appreciated upon consideration of the commercially available electronic aerosol delivery devices.

As will be discussed in more detail below, holders of aerosol delivery devices of the present disclosure may comprise some combination of a power source (e.g., an electrical power source), at least one control component (e.g., means for actuating, controlling, regulating and ceasing power, such as by controlling electrical current flow from the power source to other components of the article—e.g., a microprocessor, individually or as part of a microcontroller, a printed circuit board (PCB) that includes a microprocessor and/or microcontroller, etc.), a heating assembly configured heat a heat source and/or substrate material of a consumable unit, and a receiving chamber. Such holders may be configured to accept one or more consumable units that include a substrate material capable of yielding an aerosol upon application of sufficient heat. In some implementations, the holder may include a mouthpiece portion configured to allow drawing upon the holder for aerosol inhalation (e.g., a defined airflow path through the holder such that aerosol generated can be withdrawn therefrom upon draw).

In various aspects, the heat source of a consumable unit may be capable of generating heat to aerosolize a substrate material of the consumable unit that comprises, for example, an extruded structure and/or substrate, a substrate material associated with an aerosol precursor composition, tobacco and/or a tobacco related material, such as a material that is found naturally in tobacco that is isolated directly from the tobacco or synthetically prepared, in a solid or liquid form (e.g., beads, sheets, shreds, a wrap), or the like. As will be described in more detail below, in some implementations, an extruded structure may comprise tobacco products or a composite of tobacco with other materials such as, for example, ceramic powder. In other implementations, a tobacco extract/slurry may be loaded into porous ceramic beads. Other implementations may use non-tobacco products. In some implementations aerosol precursor composition-loaded porous beads/powders (ceramics) may be used. In other implementations, rods/cylinders made of extruded slurry of ceramic powder and aerosol precursor composition may be used.

According to certain aspects of the present disclosure, it may be advantageous to provide an aerosol delivery device that is easy to use and that provides reusable and/or replaceable components. FIG. 1 illustrates one example implementation of such a device. In particular, FIG. 1 illustrates a perspective view of an aerosol delivery device 100 that includes a holder 200 and a removable consumable unit 300, according to one implementation of the present disclosure. As shown in the figure, the holder 200 is configured to receive the removable consumable unit 300. In the depicted implementation, the holder 200 comprises a main body 202 and a mouthpiece portion 204, wherein the main body 202 defines a proximal end 206 and a distal end 208. In the depicted implementation, the mouthpiece portion 204 is located proximate the proximal end 206 of the main body 202, and more particularly, a proximal end of the mouthpiece portion 204 defines the proximal end 206 of the main body 202. In the depicted implementation, the mouthpiece portion 204 is removable from the main body 202; however, in other implementations, the mouthpiece portion may be integral with the main body.

In some implementations, the holder (or any components thereof) may be made of moldable plastic materials such as, for example, polycarbonate, polyethylene, acrylonitrile butadiene styrene (ABS), polyamide (Nylon), or polypropylene. In other implementations, the holder may be made of a different material, such as, for example, a different plastic material, a metal material (such as, but not limited to, stainless steel, aluminum, brass, copper, silver, gold, bronze, titanium, various alloys, etc), a graphite material, a glass material, a ceramic material, a natural material (such as, but not limited to, a wood material), a composite material, or any combinations thereof. As noted above, the mouthpiece portion of some implementations is separable from the main body, while in other implementations, the mouthpiece portion may be integral with the main body. In any event, the mouthpiece portion and the main body may be made of the same material or different materials. In various implementations comprising a separable mouthpiece portion, the mouthpiece portion may be coupled to the main body in a variety of ways, including, for example, via one or more of a snap-fit, interference fit, screw thread, magnetic, and/or bayonet connection. In other implementations, the mouthpiece portion may be integral with the main body and thus may not be separable.

In the depicted implementation, the holder 200 includes an opening 210 located proximate the distal end 208 and through which the consumable unit 300 is received. In the depicted implementation, the opening 210 of the holder 200 leads to a receiving chamber 212 (see FIG. 3) located within the holder 200. The holder 200 of the depicted implementation also includes an opening 215 (see FIG. 3) located proximate the proximal end 206 through which aerosol is delivered to a user. The holder 200 of the depicted implementation also includes an indicator 226 configured to provide visual indication of one or more conditions of the device 100. In various implementations, a consumable unit may be received by the holder (and in particular, the receiving chamber) into a lighting/use position. As will be described in more detail below, in the lighting/use position the heat source of the consumable unit may be ignited, and the ignited heat source and/or the inductive heating assembly may aerosolize substrate material contained therein for delivery to a user.

FIG. 2 illustrates the holder 200 and consumable unit 300 of the aerosol delivery device 100 of FIG. 1, with the consumable unit 300 being inserted in the opening 210 of the holder 200, such as to locate the consumable unit 300 into a lighting and/or use positon. In the depicted implementation, the holder 200 includes a consumable unit retention assembly configured to retain the consumable unit in the receiving chamber in the lighting/use position. In the depicted implementation, the consumable unit retention assembly comprises a magnetic retaining system comprising one or more magnets, wherein when the consumable unit 300 is pushed into and fully received within the receiving chamber 212, the consumable unit 300 is temporarily "locked" in place within the holder 200.

In other implementations, other retaining features may be used. For example, in some implementations one or more retention spheres may form part of a consumable unit retention assembly. In other implementations, a consumable unit retention assembly may comprise one or more resilient members, such as, for example, one or more O-rings, and/or other retaining features that include one or more resilient features that extend into the receiving chamber in order to engage a portion of the outer surface of the consumable unit. In other implementations, an outer housing of the consumable unit and/or the receiving chamber may include one or more protrusions and/or spring features and corresponding detent features configured to retain the consumable unit in the receiving chamber. In still other implementations, an inner surface of the receiving chamber may have a decreasing diameter (and/or one or more portions having a decreased diameter) that may be configured to retain the consumable unit in the receiving chamber. In other implementations, the holder may include actively retractable features (e.g., features that are actively retractable by a user) configured to engage the consumable unit to retain it in the receiving chamber. In other implementations, the holder may include one or more wedge features configured to engage and retain the consumable unit in the receiving chamber. In still other implementations, one or more other features of the consumable unit and/or one or more features of the holder may create a releasable connection between the receiving chamber and the consumable unit. For example, in some implementations, the consumable unit and the receiving chamber may have a releasable screw-type connection. In still other implementations, the consumable unit may be retained in the receiving chamber via a spring-loaded latching mechanism. Combinations of two or more of these retaining features may also be used.

In various implementations, one or more components of a consumable unit retention assembly may be made of any material, including for example, but not limited to, metal or plastic materials. For example, some implementations may include one or more components of a consumable unit retention assembly that are made of a metal material such as, for example, stainless steel, aluminum, brass, copper, silver, gold, bronze, titanium, various alloys, etc. In some implementations, one or more components of a consumable unit retention assembly may be made of a moldable plastic material such as, for example, polycarbonate, polyethylene, acrylonitrile butadiene styrene (ABS), polyamide (Nylon), or polypropylene. In some implementations, one or more components of a consumable unit retention assembly may be made of a different material, such as, for example, a different plastic material, a different metal material, a graphite material, a glass material, a ceramic material, a natural material (such as, but not limited to, a wood material), a composite material, or any combinations thereof.

FIG. 3 illustrates the holder 200 and consumable unit 300 of the aerosol delivery device 100 of FIG. 1, with the consumable unit 300 located in a lighting/use position. In the lighting/use position of the depicted implementation, the consumable unit 300 is located inside of the holder 200. In particular, in the lighting/use position of the depicted implementation, the distal end of the consumable unit 300 is configured to be proximate the distal end 208 of the holder 200. In the lighting/use position of other implementations, however, a consumable unit may be received into the holder to varying degrees so long as the heat source is configured be ignited (directly or indirectly) by the heating assembly. As will be described in more detail below, in the lighting/use position an inductive heating assembly is configured to ignite the heat source of the consumable unit 300.

Although not depicted in the figures, the holder of some implementations may include one or more apertures therein for allowing entrance of ambient air to be directed into the receiving chamber and/or the aerosol passageway (such as, for example, through the substrate consumable unit and/or downstream from the substrate consumable unit). Thus, when a user draws on the holder (e.g., via the mouthpiece portion thereof), air may be drawn into the receiving chamber and/or the aerosol passageway for inhalation by the user.

As noted, the holder of the aerosol delivery device of various implementations of the present disclosure includes an inductive heater configured to ignite the heat source of a consumable unit. In some implementations, the inductive heater is also configured to heat at least a portion of the substrate material of the consumable unit. In such implementations, the inductive heater of present disclosure may supplement heating of the substrate material provided by the heat source. FIG. 3 illustrates a schematic view of the holder 200 and consumable unit 300 of the aerosol delivery device 100. In the depicted implementation, the inductive heater comprises an inductive heating assembly 220. As will be described in more detail below, the inductive heating assembly of various implementations is configured to inductively ignite the ignitable heat source of the consumable unit. The holder 200 of the depicted implementation further includes a control component 222 (e.g., a microprocessor, individually or as part of a microcontroller, a printed circuit board (PCB) that includes a microprocessor and/or microcontroller, etc.), a power source 224 (e.g., a battery, which may be rechargeable, and/or a rechargeable supercapacitor), a manually actuatable button 225, an indicator 226 (e.g., a light emitting diode (LED)), and an aerosol passage 228 that extends from the receiving chamber 212, through the main body 202, and out through the opening 215 in the mouthpiece portion 204.

In some implementations, the holder may be characterized as being disposable in that the holder may be configured for only a limited number of uses (e.g., until a battery power component no longer provides sufficient power to the article) with a limited number of consumable units and, thereafter, the entire device, including the holder, may be discarded. In other implementations, the holder may have a replaceable power source (e.g., a replaceable battery) such that the holder may be reused through a number of power source exchanges and with many consumable units. Similarly, the holder may be rechargeable and thus may be combined with any type of recharging technology. For example, the holder may have a replaceable battery or a rechargeable battery, solid-state battery, thin-film solid-state battery, rechargeable supercapacitor or the like, and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Pat. App. Pub. No. 2017/0112196 to Sur et al., which is incorporated herein by reference in its entirety. Further, in some implementations, the mouthpiece portion may comprise a single-use device. A single use component for use with a control body is disclosed in U.S. Pat. No. 8,910,639 to Chang et al., which is incorporated herein by reference in its entirety. In some implementations, the holder may be inserted into and/or coupled with a separate charging station for charging a rechargeable battery of the device. In some implementations, the charging station itself may include a rechargeable power source that recharges the rechargeable battery of the device.

Some additional examples of possible power sources are described in U.S. Pat. No. 9,484,155 to Peckerar et al., and U.S. Pat. App. Pub. No. 2017/0112191 to Sur et al., filed Oct. 21, 2015, the disclosures of which are incorporated herein by reference in their respective entireties. Reference also is made to the control schemes described in U.S. Pat. No. 9,423,152 to Ampolini et al., which is incorporated herein by reference in its entirety. In one implementation, the indicator 226 may comprise one or more light emitting diodes, quantum dot-based light emitting diodes or the like. The indicator 226 can be in communication with the control component 222 and be illuminated, for example, when the heating assembly is active and/or when a consumable unit is received in the receiving chamber 212 of the housing 200.

As noted, the inductive heating assembly 220 of the depicted implementation is configured to ignite the ignitable heat source 308 of the consumable unit 300. In some implementations, the inductive heating assembly may also be configured to heat at least a portion of the substrate material of the removable consumable unit. In such a manner, inductive heating of the substrate material may supplement heating of the substrate material provided by the heat source. In various implementations, the inductive heating assembly may comprise a resonant transmitter configured to interact with at least one resonant receiver (e.g., one or more susceptor materials). In such a manner, the heat source of a consumable unit of the present disclosure may be ignited, and a portion of the substrate material of the consumable unit may be heated, by directing alternating current to the at least one resonant transmitter to produce an oscillating magnetic field in order to induce eddy currents in the at least one resonant receiver. In some implementations, a first portion of the inductive heating assembly may be configured to heat the heat source and a second portion of the inductive heating assembly may be configured to heat the substrate material.

In the depicted implementation, the heat source 308 is ignited using the inductive heating assembly 220. In particular, the heat source 308 of the depicted implementation comprises the resonant receiver, and alternating current imparted into the susceptor material of the heat source will generate heat thereby igniting the ignitable heat source. It should be noted that in other implementations various other configurations are possible. For example, in another implementation the outer housing of the consumable unit, or a portion thereof, may comprise the resonant receiver and/or may serve as a common resonant receiver for the heat source.

Examples of various inductive heating methods and configurations are described in U.S. Pat. App. Pub. No. 2019/0124979 to Sebastian et al., which is incorporated by reference herein in its entirety. Further examples of various induction-based control components and associated circuits are described in U.S. Pat. App. Pub. No. 2018/0132531 to Sur et al., and U.S. Patent App. Pub. No. 2017/0202266 to Sur et al., each of which is incorporated herein by reference in its entirety.

Although in various implementations the resonant transmitter may have a variety of forms, in the depicted implementation the resonant transmitter comprises an induction coil 230 (such as, but not limited to, a helical coil having any number of turns) that surrounds a support cylinder 232 and extends the full length of the receiving chamber 212. It should be noted that in other implementations, there need not be a support cylinder. In various implementations, the resonant transmitter may be made of one or more conductive materials, including, for example, silver, gold, aluminum, brass, zinc, iron, nickel, and alloys of thereof, conductive ceramics e.g., yttrium-doped zirconia, indium tin oxide, yttrium doped titanate, etc, and any combination of the above. In the depicted implementation, the induction coil 230 is made of a conductive metal material, such as copper. In further implementations, the induction coil may include a nonconductive insulating cover/wrap material. Such materials may include, for example, one or more polymeric materials, such as epoxy, silicon rubber, etc., which may be helpful for low temperature applications, or fiberglass, ceramics, refractory materials, etc., which may be helpful for high temperature applications.

It should be noted that although the depicted implementation describes a single resonant transmitter, in other implementations, there may be multiple independent resonant transmitters or transmitter portions, including, for example, implementations having segmented inductive heating arrangements. In such a manner, for example, the inductive heater portion may comprise a first portion configured to heat the ignitable heat source, and a second portion configured to heat the substrate material (or a portion thereof). For example, in some implementations the inductor coil may have one segment positioned proximate the heat source and configured to inductively ignite the heat source, and another segment positioned proximate the substrate material and configured to heat (e.g., as a supplement to the heat provided by the heat source) the substrate material.

As noted, a change in current in the resonant transmitter (e.g., an induction coil), as directed thereto from the power source by the control component (e.g., via a driver circuit) may produce an alternating electromagnetic field that penetrates the susceptor material(s), thereby generating electrical eddy currents within the susceptor material(s). In some implementations, the alternating electromagnetic field may be produced by directing alternating current to the resonant transmitter. In some implementations, the control component may include an inverter or inverter circuit configured to transform direct current provided by the power source to alternating current that is provided to the resonant transmitter. As such, the resonant transmitter and the heat source of a consumable unit may be positioned proximate each other in order to ignite the heat source or a portion thereof by inductive heating.

The eddy currents flowing in the susceptor material(s) may generate heat through the Joule effect, wherein the amount of heat produced is proportional to the square of the electrical current times the electrical resistance of the susceptor material. For implementations wherein the susceptor material comprises ferromagnetic materials, heat may also be generated by magnetic hysteresis losses. Several factors may contribute to the temperature rise of the susceptor material including, but not limited to, proximity to the resonant transmitter, distribution of the magnetic field, electrical resistivity of the material of the susceptor component, saturation flux density, skin effects or depth, hysteresis losses, magnetic susceptibility, magnetic permeability, and dipole moment of the material.

In the depicted implementation, the support cylinder 232 defines the receiving chamber 212. In other implementations, however, the support cylinder need not define the receiving chamber, and the receiving chamber may have other forms. For example, in some implementations, the receiving chamber may comprise a rotatable door, a siding tray, etc. In various implementations, the shape of the receiving chamber may be configured to accommodate one or more different cross-section shapes of a consumable unit. For example, in some implementations in which the consumable unit has a substantially round cross-section shape, the receiving chamber may have a substantially cylindrical shape, etc.

In the depicted implementation, the resonant transmitter 230 substantially surrounds the receiving chamber 212, which is configured to receive the consumable unit 300. In the depicted implementation, the induction coil 230 defines a generally tubular configuration. In some implementations, the support cylinder 232 may also define a tubular configuration and may be configured to support the induction coil 230 such that the induction coil 230 does not contact the consumable unit. As such, in some implementations the support cylinder 232 may comprise a nonconductive material, which may be substantially transparent to an oscillating magnetic field produced by the induction coil 230. In various implementations, the induction coil 230 may be imbedded in, or otherwise coupled to, the support cylinder 232. In the illustrated implementation, the induction coil 230 is engaged with an outer surface of the support cylinder 232; however, in other implementations, the coil may be positioned at an inner surface of the support cylinder, be fully imbedded in the support cylinder, or have some other configuration. In some implementations, the inductive heating assembly 220 is activated automatically when the consumable unit 300 is received in the receiving chamber 212. This may be accomplished, for example, via a sensor 234 configured to send a signal to the control component 222 upon sensing that the consumable unit 300 is fully received in the receiving chamber 212. In other implementations, however, other methods of determining the presence of the consumable unit may be used, and a consumable unit need not be fully received in the receiving chamber in order to activate the inductive heating assembly. In still other implementations, activation of the inductive heating assembly may occur manually. For example, in some implementations activation of the inductive heating assembly may occur via actuation of an input element, such as, for example, a button.

In some implementations, other input elements may be included (which may replace or supplement a consumable unit sensor, and/or a manually actuated button configured to activate the heating assembly). Any component or combination of components may be utilized as an input for controlling the function of the device. For example, one or more pushbuttons may be used as described in U.S. Pub. No. 2015/0245658 to Worm et al., which is incorporated herein by reference in its entirety. Likewise, a touchscreen may be used as described in U.S. Pat. App. Pub. No. 2016/0262454, to Sears et al., which is incorporated herein by reference in its entirety. As a further example, components adapted for gesture recognition based on specified movements of the aerosol delivery device may be used as an input. See U.S. Pat. App. Pub. No. 2016/0158782 to Henry et al., which is incorporated herein by reference in its entirety. As still a further example, a capacitive sensor may be implemented on the aerosol delivery device to enable a user to provide input, such as by touching a surface of the device on which the capacitive sensor is implemented.

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties.

Other suitable current actuation/deactuation mechanisms may include a temperature actuated on/off switch or a lip pressure actuated switch, or a touch sensor (e.g., capacitive touch sensor) configured to sense contact between a user (e.g., mouth or fingers of user) and one or more surfaces of the aerosol delivery device. An example mechanism that can provide such puff-actuation capability includes a Model 163PC01D36 silicon sensor, manufactured by the MicroSwitch division of Honeywell, Inc., Freeport, Ill. With such sensor, the heating member may be activated rapidly by a change in pressure when the user draws on the device. In addition, flow sensing devices, such as those using hot-wire anemometry principles, may be used to cause the energizing of the heating assembly sufficiently rapidly after sensing a change in airflow. A further puff actuated switch that may be used is a pressure differential switch, such as Model No. MPL-502-V, range A, from Micro Pneumatic Logic, Inc., Ft. Lauderdale, Fla. Another suitable puff actuated mechanism is a sensitive pressure transducer (e.g., equipped with an amplifier or gain stage) which is in turn coupled with a comparator for detecting a predetermined threshold pressure. Yet another suitable puff actuated mechanism is a vane which is deflected by airflow, the motion of which vane is detected by a movement sensing means. Yet another suitable actuation mechanism is a piezoelectric switch. Also useful is a suitably connected Honeywell MicroSwitch Microbridge Airflow Sensor, Part No. AWM 2100V from MicroSwitch Division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Other suitable differential switches, analog pressure sensors, flow rate sensors, or the like, will be apparent to the skilled artisan with the knowledge of the present disclosure. In some implementations, a pressure-sensing tube or other passage providing fluid connection between the puff actuated switch and substrate tablet may be included in the housing so that pressure changes during draw are readily identified by the switch. Other example puff actuation devices that may be useful according to the present disclosure are disclosed in U.S. Pat. Nos. 4,922,901, 4,947,874, and 4,947,874, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties.

Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. Pat. App. Pub. No. 2017/0099877, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various implementations, and all of the foregoing disclosures are incorporated herein by reference in their entireties.

FIG. 4 illustrates a perspective view of the removable consumable unit 300, according to an example implementation of the present disclosure. In the depicted implementation, the consumable unit 300 defines a first end 302 and a distal end 304. The consumable unit 300 of the depicted implementation further includes a heat portion 306 (which comprises a heat source 308), a substrate portion 310 (which comprises a substrate material 316), and a substrate container in the form of an outer housing 312 configured to circumscribe the heat source 308 and the substrate material 316. It should be noted that although in the depicted implementation the consumable unit 300 has a substantially cylindrical overall shape, in various other implementations, the consumable unit or any of its components, may have a different shape. For example, in some implementations the consumable unit (and/or any of its components) may have a substantially rectangular shape, such as a substantially rectangular cuboid shape. In other implementations, the consumable unit (and/or any of its components) may have other hand-held shapes. Some examples of consumable unit configurations that may be applicable to the present disclosure can be found in U.S. Pat. App. Pub. No. 2021/0015173 to Cox et al., which is incorporated herein by reference in its entirety.

In some implementations, a barrier may exist between the heat source and the substrate material. In some implementations, such a barrier may comprise a disc that may include one or more apertures therethrough. In some implementations, the barrier may be constructed of a metal material (such as, for example, stainless steel, aluminum, brass, copper, silver, gold, bronze, titanium, various alloys, etc.), or a graphite material, or a ceramic material, or a plastic material, or any combinations thereof. In some implementations, a heat transfer component, which may or may not comprise a barrier, may exist between the heat source and the substrate material. Some examples of heat transfer components are described in U.S. Pat. App. Pub. No. 2019/0281891 to Hejazi et al., which is incorporated herein by reference in its entirety. In some implementations, a barrier and/or a heat transfer component may prevent or inhibit combustion gasses from being drawn through the substrate material (and/or from being drawn through air passageways through which aerosol is drawn).

In various implementations, the heat source may be configured to generate heat upon ignition thereof. In the depicted implementation, the heat source 308 comprises a combustible fuel element that has a generally cylindrical shape and that incorporates a combustible carbonaceous material. In other implementations, the heat source may have a different shape, for example, a prism shape having a cubic or hexagonal cross-section. Carbonaceous materials generally have a high carbon content. Some carbonaceous materials may be composed predominately of carbon, and/or typically have carbon contents of greater than about 60 percent, generally greater than about 70 percent, often greater than about 80 percent, and frequently greater than about 90 percent, on a dry weight basis.

As noted above, the heat source 308 of the consumable unit 300 of the depicted implementation comprises a susceptor material configured to be heated by the resonant transmitter. In some implementations, the heat source material itself (e.g., a carbon material) may comprise a susceptor material. In other implementations, a susceptor material may be added to the heat source. In some implementations, the susceptor material may comprise a ferromagnetic material including, but not limited to, cobalt, iron, nickel, zinc, manganese, and any combinations thereof. In some implementations, one or more of the susceptor components may be made of other materials, including, for example, other metal materials such as aluminum or stainless steel, as well as ceramic materials such as silicon carbide, and combinations of materials. In still other implementations, the susceptor material may comprise other conductive materials including metals such as copper, alloys of materials, or other materials with one or more susceptor materials imbedded therein. In some implementations, the susceptor material may comprise a granulated susceptor component, including, but not limited to a shredded susceptor material. In other implementations, a granulated susceptor component may comprise susceptor particles, susceptor beads, etc.

In some instances, the heat source may incorporate elements other than combustible carbonaceous materials (e.g., tobacco components, such as powdered tobaccos or tobacco extracts; flavoring agents; salts, such as sodium chloride, potassium chloride and sodium carbonate; heat stable graphite a hollow cylindrical (e.g., tube) fibers; iron oxide powder; glass filaments; powdered calcium carbonate; alumina granules; ammonia sources, such as ammonia salts; and/or binding agents, such as guar gum, ammonium alginate and sodium alginate). In other implementations, the heat source may comprise a plurality of ignitable objects, such as, for example, a plurality of ignitable beads. It should be noted that in other implementations, the heat source may differ in composition or relative content amounts from those listed above. For example, in some implementations different forms of carbon could be used as a heat source, such as graphite or graphene. In other implementations, the heat source may have increased levels of activated carbon, different porosities of carbon, different amounts of carbon, blends of any above mentioned components, etc. In still other implementations, the heat source may comprise a non-carbon heat source, such as, for example, a combustible liquefied gas configured to generate heat upon ignition thereof. For example, in some implementations, the liquefied gas may comprise one or more of petroleum gas (LPG or LP-gas), propane, propylene, butylenes, butane, isobutene, methyl propane, or n-butane. In still other implementations, the heat source may comprise a chemical reaction based heat source, wherein ignition of the heat source comprises the interaction of two or more individual components. For example, a chemical reaction based heat source may comprise metallic agents and an activating solution, wherein the heat source is activated when the metallic agents and the activating solution come in contact. Some examples of chemical based heat sources can be found in U.S. Pat. No. 7,290,549 to Banerjee et al., which is incorporated herein by reference in its entirety. Combinations of heat sources are also possible. Although specific dimensions of an applicable heat source may vary, in some implementations, the heat source may have a length in an inclusive range of approximately 5 mm to approximately 20 mm, and in some implementations may be approximately 12 mm, and an overall diameter in an inclusive range of approximately 3 mm to approximately 8 mm, and in some implementations may be approximately 4.8 mm (and in some implementations, approximately 7 mm).

Although in other implementations the heat source may be constructed in a variety of ways, in the depicted implementation, the heat source 308 is extruded or compounded using a ground or powdered carbonaceous material, and has a density that is greater than about 0.5 g/cm$^3$, often greater than about 0.7 g/cm$^3$, and frequently greater than about 1 g/cm$^3$, on a dry weight basis. See, for example, the types of fuel source components, formulations and designs set forth in U.S. Pat. No. 5,551,451 to Riggs et al. and U.S. Pat. No. 7,836,897 to Borschke et al., which are incorporated herein by reference in their entireties.

In various implementations the heat source may have a variety of forms, including, for example, a substantially solid cylindrical shape or a hollow cylindrical (e.g., tube) shape. In other implementations, the heat source may comprise a plurality of hollow or substantially solid spheres, which in some implementations may comprise substantially the same size, and in other implementations may comprise more than one size. In various implementations, the heat source may be made in variety of ways, including, but not limited to, via extrusion, injection molding, compression molding, etc. The heat source 308 of the depicted implementation comprises an extruded monolithic carbonaceous material that has a generally cylindrical shape that includes a plurality of internal passages 314 (see FIG. 5) extending longitudinally from a first end of the heat source 308 to an opposing second end of the heat source 308.

In the depicted implementation, the outer housing 312 is configured to circumscribe the entire heat source 308 and substrate material 316. In other implementations, however, the outer housing may circumscribe only a portion of the heat source such that the remaining portion is exposed. In the depicted implementation, the outer housing 312 of the consumable unit 300 includes a plurality of end openings 315 and peripheral openings 317 located on the end of the outer housing 312 proximate the heat source 308. Although in other implementations the size and shape of the end and peripheral openings may differ, the end openings 315 of the depicted implementation comprise a plurality of elongate rounded slots radially extending from a central area of the end of the outer housing 312, and the peripheral openings 317 comprise a plurality of aligned rows of substantially circular openings. In the depicted implementation, one or more of the end openings 315 are in fluid communication with one or more of the internal passages 314 of the heat source 308. It should be noted that in other implementations, there need not be a plurality of internal passages and/or the plurality of internal passages may take other forms and/or sizes. For example, in some implementations, there may be as few as two internal passages, and still other implementations may include as few as a single internal passage. Still other implementations may include no internal passages at all. Additional implementations may include multiple internal passages that may be of unequal diameter and/or shape and which may be unequally spaced and/or located within the heat source.

Some implementations may alternatively, or additionally, include one or more peripheral grooves that extend longitudinally from a first end of the heat source to an opposing second end, although in other implementations the grooves need not extend the full length of the heat source. In some implementations, such grooves may be substantially equal in width and depth and may be substantially equally distributed about a circumference of the heat source. In such implementations, there may be as few as two grooves, and still other implementations may include as few as a single groove. Still other implementations may include no grooves at all. Additional implementations may include multiple grooves that may be of unequal width and/or depth, and which may be unequally spaced around a circumference of the heat source. In still other implementations, the heat source may include flutes and/or slits extending longitudinally from a first end of the extruded monolithic carbonaceous material to an opposing second end thereof. In some implementations, the heat source may comprise a foamed carbon monolith formed in a foam process of the type disclosed in U.S. Pat. No. 7,615,184 to Lobovsky, which is incorporated herein by reference in its entirety. As such, some implementations may provide advantages with regard to reduced time taken to ignite the heat source. In some other implementations, the heat source may be co-extruded with a layer of insulation (not shown), thereby reducing manufacturing time and expense. Other implementations of fuel elements include carbon fibers of the type described in U.S. Pat. No. 4,922,901 to Brooks et al. or other heat source implementations such as is disclosed in U.S. Pat. App. Pub. No. 2009/0044818 to Takeuchi et al., each of which is incorporated herein by reference in its entirety. Further examples of heat sources including debossed heat source systems, methods, and smoking articles that include such heat sources are disclosed in U.S. Pat. App. Pub. No. 2019/0254335 to Spicer et al., which is incorporated herein by reference in its entirety.

Generally, the heat source is positioned sufficiently near an aerosol delivery component (e.g., a substrate portion comprising a substrate material) having one or more aerosolizable components so that the aerosol formed/volatilized by the application of heat from the heat source to the aerosolizable components (as well as any flavorants, medicaments, and/or the like that are likewise provided for delivery to a user) is deliverable to the user by way of the mouthpiece. That is, when the heat source heats the substrate material, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof. Additionally, the selection of various smoking article elements is appreciated upon consideration of commercially available electronic smoking articles, such as those representative products listed in the background art section of the present disclosure.

FIG. 5 illustrates a longitudinal cross-section view of the consumable unit 300 of FIG. 4. As shown in the figure, the substrate material 316 of the depicted implementation has opposed first and second ends, with the heat source 308 disposed adjacent the first end of the substrate material 316. Although dimensions and cross-section shapes of the various components of the consumable unit may vary due to the needs of a particular application, in the depicted implementation the consumable unit 300 may have an overall length in an inclusive range of approximately 10 mm to approximately 50 mm and a diameter in an inclusive range of approximately 2 mm to approximately 20 mm. In addition, in the depicted implementation the outer housing 312 may have a thickness in the inclusive range of approximately 0.05 mm to 0.5 mm. Furthermore, in the depicted implementation the substrate portion 310 may have a length in the inclusive range of approximately 5 mm to 30 mm and a diameter slightly less than that of the overall consumable unit in order to accommodate the thickness of the housing 312, such as, for example, a diameter in an inclusive range of approximately 2.9 mm to approximately 9.9 mm. In the depicted implementation, the substrate material 316 comprises tobacco beads, which may have diameter sizes in range of approximately 0.5 mm to 2.0 mm, although in other implementations the size may differ. In other implementations, the substrate material may be a granulated tobacco material or cut filler tobacco. Although other implementations may differ, in the depicted implementation the outer housing 312 of the consumable unit 300 is filled to about 60-90% capacity to allow for insertion of the heat source 308.

In the depicted implementation, the substrate portion 310 comprises a substrate material 316 having a single segment, although in other implementations the substrate portion may include one or more additional substrate material segments. For example, in some implementations, the aerosol delivery device may further comprise a second substrate material segment (not shown) having opposed first and second ends. In various implementations, one or more of the substrate materials may include a tobacco or tobacco related material, with an aerosol precursor composition associated therewith. In other implementations, non-tobacco materials may be used, such as a cellulose pulp material. In other implementations, the non-tobacco substrate material may not be a plant-derived material. Other possible compositions, components, and/or additives for use in a substrate material (and/or substrate materials) are described in more detail below. It should be noted that the subsequent discussion should be applicable any substrate material usable in the smoking articles described herein (such as, for example, the substrate material 316 of the depicted implementation).

In various implementations, ignition of the heat source of a consumable unit heats the heat source, which in turn heats the substrate material. In some implementations, the substrate material is also heated via the inductive heating assembly, with such heating occurring before and/or during and/or after heating of the substrate material by the heat source. Heating of the substrate material results in aerosolization of the aerosol precursor composition associated with the substrate material. As noted, in various implementations the holder may include an aerosol passageway that extends therethrough. In the depicted implementation, the aerosol passageway 228 (see FIG. 3) extends from the receiving chamber 212 through the main body 202 and mouthpiece portion 204 of the holder 200. As such, upon a draw applied to the mouthpiece portion 204 of the holder 200, aerosol generated by the consumable unit 300 is configured to be delivered to a user. In some implementations, the aerosol passageway extends from the receiving chamber to the mouthpiece portion of the holder in a substantially direct path. For example, in some implementations, the aerosol passageway may extend from the receiving chamber through the holder along a path that is aligned with, or substantially parallel to, a longitudinal axis thereof. In other implementations, however, the aerosol passageway may have a less direct route. For example, the aerosol passageway of some implementations may define an indirect route from the receiving chamber through the holder, such as, for example, via one or more tortuous paths. In some implementations, for example, such a path may allow the aerosol to cool before reaching a user. In some implementations, such a path may allow mixing of the aerosol with air from outside of the holder. In some implementations, such a path may comprise a serpentine pattern. In other implementations, such a path may include one or more sections that overlap and/or double back toward each other. In other implementations, such a path may comprise one or more spiral turns that extend around an inner diameter of the holder. Other implementations may include combinations of tortuous aerosol paths. Still other implementations may include combinations of direct and tortuous path sections.

In some implementations, the mouthpiece portion, or other portion of the holder may include a filter configured to receive the aerosol therethrough in response to the draw applied to the holder. In various implementations, the filter may be provided, in some aspects, as a circular disc radially and/or longitudinally disposed proximate the end of the holder opposite the receiving end. In this manner, upon a draw on the holder, the filter may receive the aerosol flowing through holder. In some implementations, the filter may comprise discrete segments. For example, some implementations may include a segment providing filtering, a segment providing draw resistance, a hollow segment providing a space for the aerosol to cool, other filter segments, and any one or any combination of the above. In some implementations, the mouthpiece portion may include a filter that may also provide a flavorant additive. In some implementations, a filter may include one or more filter segments that may be replaceable. For example, in some implementations one or more filter segments may be replaceable in order to customize a user's experience with the device, including, for example, filter segments that provide different draw resistances and/or different flavors. Some examples of flavor adding materials and/or components configured to add a flavorant can be found in U.S. patent application Ser. No. 16/408,942, filed on May 10, 2019 and titled Flavor Article for an Aerosol Delivery Device; U.S. Pat. App. Pub. No. 2019/0289909 to Hejazi; and U.S. Pat. App. Pub. No. 2020/0288787 to Hejazi, each of which is incorporated by reference herein in its entirety.

Preferably, the elements of the substrate material do not experience thermal decomposition (e.g., charring, scorching, or burning) to any significant degree, and the aerosolized components are entrained in the air drawn through the smoking article, including a filter (if present), and into the mouth of the user. In the consumable unit 300 of the depicted implementation, the substrate material 316 comprises a plurality of tobacco beads that are contained in the substantially cylindrical outer housing 312. In various implementations, however, the substrate material may comprise a variety of different compositions and combinations thereof, as explained in more detail below.

In various implementations, the substrate material may comprise a tobacco material, a non-tobacco material, or a combination thereof. In one implementation, for example, the substrate material may comprise a blend of flavorful and aromatic tobaccos in cut filler form. In another implementation, the substrate material may comprise a reconstituted tobacco material, such as described in U.S. Pat. No. 4,807,809 to Pryor et al.; U.S. Pat. No. 4,889,143 to Pryor et al. and U.S. Pat. No. 5,025,814 to Raker, the disclosures of which are incorporated herein by reference in their entirety. Additionally, a reconstituted tobacco material may include a reconstituted tobacco paper for the type of cigarettes described in Chemical and Biological Studies on New Cigarette Prototypes that Heat Instead of Burn Tobacco, R. J. Reynolds Tobacco Company Monograph (1988), the contents of which are incorporated herein by reference in its entirety. For example, a reconstituted tobacco material may include a sheet-like material containing tobacco and/or tobacco-related materials. As such, in some implementations, the substrate material may be formed from a wound roll of a reconstituted tobacco material. In another implementation, the substrate material may be formed from shreds, strips, and/or the like of a reconstituted tobacco material. In another implementation, the tobacco sheet may comprise overlapping layers (e.g., a gathered web), which may, or may not, include heat conducting constituents. Examples of substrate portions that include a series of overlapping layers (e.g., gathered webs) of an initial substrate sheet formed by the fibrous filler material, aerosol forming material, and plurality of heat conducting constituents are described in U.S. Pat. App. Pub. No. 2019/0261685 to Sebastian et al., which is incorporated herein by reference in its entirety.

In some implementations, the substrate material may include a plurality of microcapsules, beads, granules, and/or the like having a tobacco-related material. For example, a representative microcapsule may be generally spherical in shape, and may have an outer cover or shell that contains a liquid center region of a tobacco-derived extract and/or the like. In some implementations, one or more of the substrate materials may include a plurality of microcapsules each formed into a hollow cylindrical shape. In some implementations, one or more of the substrate materials may include a binder material configured to maintain the structural shape and/or integrity of the plurality of microcapsules formed into the hollow cylindrical shape.

Tobacco employed in one or more of the substrate materials may include, or may be derived from, tobaccos such as flue-cured tobacco, burley tobacco, Oriental tobacco, Maryland tobacco, dark tobacco, dark-fired tobacco and Rustica tobacco, as well as other rare or specialty tobaccos, or blends thereof. Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 6,730,832 to Dominguez et al.; U.S. Pat. No. 7,011,096 to Li et al.; U.S. Pat. No. 7,017,585 to Li et al.; U.S. Pat. No. 7,025,066 to Lawson et al.; U.S. Pat. App. Pub. No. 2004/0255965 to Perfetti et al.; PCT Pub. No. WO 02/37990 to Bereman; and Bombick et al., *Fund. Appl. Toxicol.,* 39, p. 11-17 (1997); the disclosures of which are incorporated herein by reference in their entireties.

In still other implementations of the present disclosure, the substrate material may include an extruded structure that includes, or is essentially comprised of a tobacco, a tobacco related material, glycerin, water, and/or a binder material, although certain formulations may exclude the binder material. In various implementations, suitable binder materials may include alginates, such as ammonium alginate, propylene glycol alginate, potassium alginate, and sodium alginate. Alginates, and particularly high viscosity alginates, may be employed in conjunction with controlled levels of free calcium ions. Other suitable binder materials include hydroxypropylcellulose such as Klucel H from Aqualon Co.; hydroxypropylmethylcellulose such as Methocel K4MS from The Dow Chemical Co.; hydroxyethylcellulose such as Natrosol 250 MRCS from Aqualon Co.; microcrystalline cellulose such as Avicel from FMC; methylcellulose such as Methocel A4M from The Dow Chemical Co.; and sodium carboxymethyl cellulose such as CMC 7HF and CMC 7H4F from Hercules Inc. Still other possible binder materials include starches (e.g., corn starch), guar gum, carrageenan, locust bean gum, pectins and xanthan gum. In some implementations, combinations or blends of two or more binder materials may be employed. Other examples of binder materials are described, for example, in U.S. Pat. No. 5,101,839 to Jakob et al.; and U.S. Pat. No. 4,924,887 to Raker et al., each of which is incorporated herein by reference in its entirety. In some implementations, the aerosol forming material may be provided as a portion of the binder material (e.g., propylene glycol alginate). In addition, in some implementations, the binder material may comprise nanocellulose derived from a tobacco or other biomass.

In some implementations, the substrate material may include an extruded material, as described in U.S. Pat. App. Pub. No. 2012/0042885 to Stone et al., which is incorporated herein by reference in its entirety. In yet another implementation, the substrate material may include an extruded structure and/or substrate formed from marumarized and/or non-marumarized tobacco. Marumarized tobacco is known, for example, from U.S. Pat. No. 5,105,831 to Banerjee, et al., which is incorporated by reference herein in its entirety. Marumarized tobacco includes about 20 to about 50 percent (by weight) tobacco blend in powder form, with glycerol (at about 20 to about 30 percent weight), calcium carbonate (generally at about 10 to about 60 percent by weight, often at about 40 to about 60 percent by weight), along with binder agents, as described herein, and/or flavoring agents. In various implementations, the extruded material may have one or more longitudinal openings.

In various implementations, the substrate material may take on a variety of conformations based upon the various amounts of materials utilized therein. For example, a sample substrate material may comprise up to approximately 98% by weight, up to approximately 95% by weight, or up to approximately 90% by weight of a tobacco and/or tobacco related material. A sample substrate material may also comprise up to approximately 25% by weight, approximately 20% by weight, or approximately 15% by weight water—particularly approximately 2% to approximately 25%, approximately 5% to approximately 20%, or approximately 7% to approximately 15% by weight water. Flavors and the like (which include, for example, medicaments, such as nicotine) may comprise up to approximately 10%, up to about 8%, or up to about 5% by weight of the aerosol delivery component.

Additionally, or alternatively, the substrate material may include an extruded structure and/or a substrate that includes or essentially is comprised of tobacco, glycerin, water, and/or binder material, and is further configured to substantially maintain its structure throughout the aerosol-generating process. That is, the substrate material may be configured to substantially maintain its shape (e.g., the substrate material does not continually deform under an applied shear stress) throughout the aerosol-generating process. Although such an example substrate material may include liquids and/or some moisture content, the substrate may remain substantially solid throughout the aerosol-generating process and may substantially maintain structural integrity throughout the aerosol-generating process. Example tobacco and/or tobacco related materials suitable for a substantially solid substrate material are described in U.S. Pat. App. Pub. No. 2015/0157052 to Ademe et al.; U.S. Pat. App. Pub. No. 2015/0335070 to Sears et al.; U.S. Pat. No. 6,204,287 to White; and U.S. Pat. No. 5,060,676 to Hearn et al., which are incorporated herein by reference in their entirety.

In some implementations, the amount of substrate material used within the smoking article may be such that the article exhibits acceptable sensory and organoleptic properties, and desirable performance characteristics. For example, in some implementations an aerosol precursor composition such as, for example, glycerin and/or propylene glycol, may be employed within the substrate material in order to provide for the generation of a visible mainstream aerosol that in many regards resembles the appearance of tobacco smoke. For example, the amount of aerosol precursor composition incorporated into the substrate material of the smoking article may be in the range of about 3.5 grams or less, about 3 grams or less, about 2.5 grams or less, about 2 grams or less, about 1.5 grams or less, about 1 gram or less, or about 0.5 gram or less.

According to another implementation, a smoking article according to the present disclosure may include a substrate material comprising a porous, inert material such as, for example, a ceramic material. For example, in some implementations ceramics of various shapes and geometries (e.g., beads, rods, tubes, etc.) may be used, which have various pore morphology. In addition, in some implementations non-tobacco materials, such as an aerosol precursor composition, may be loaded into the ceramics. In another implementation, the substrate material may include a porous, inert material that does not substantially react, chemically and/or physically, with a tobacco-related material such as, for example, a tobacco-derived extract. In addition, an extruded tobacco, such as those described above, may be porous. For example, in some implementations an extruded tobacco material may have an inert gas, such as, for example, nitrogen, that acts as a blowing agent during the extrusion process.

As noted above, in various implementations one or more of the substrate materials may include a tobacco, a tobacco component, and/or a tobacco-derived material that has been treated, manufactured, produced, and/or processed to incorporate an aerosol precursor composition (e.g., humectants such as, for example, propylene glycol, glycerin, and/or the like) and/or at least one flavoring agent, as well as a flame/burn retardant (e.g., diammonium phosphate and/or another salt) configured to help prevent ignition, pyrolysis, combustion, and/or scorching of the substrate material by the heat source. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties.

As noted, in some implementations, flame/burn retardant materials and other additives that may be included within one or more of the substrate materials and may include organo-phosophorus compounds, borax, hydrated alumina, graphite, potassium tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides are suitable but are not preferred agents. In each aspect of flame-retardant, burn-retardant, and/or scorch-retardant materials used in the substrate material and/or other components (whether alone or in combination with each other and/or other materials), the desirable properties most preferably are provided without undesirable off-gassing or melting-type behavior.

According to other implementations of the present disclosure, the substrate material may also incorporate tobacco additives of the type that are traditionally used for the manufacture of tobacco products. Those additives may include the types of materials used to enhance the flavor and aroma of tobaccos used for the production of cigars, cigarettes, pipes, and the like. For example, those additives may include various cigarette casing and/or top dressing components. See, for example, U.S. Pat. No. 3,419,015 to Wochnowski; U.S. Pat. No. 4,054,145 to Berndt et al.; U.S. Pat. No. 4,887,619 to Burcham, Jr. et al.; U.S. Pat. No. 5,022,416 to Watson; U.S. Pat. No. 5,103,842 to Strang et al.; and U.S. Pat. No. 5,711,320 to Martin; the disclosures of which are incorporated herein by reference in their entireties. Some casing materials may include water, sugars and syrups (e.g., sucrose, glucose and high fructose corn syrup), humectants (e.g. glycerin or propylene glycol), and flavoring agents (e.g., cocoa and licorice). Those added components may also include top dressing materials (e.g., flavoring materials, such as menthol). See, for example, U.S. Pat. No. 4,449,541 to Mays et al., the disclosure of which is incorporated herein by reference in its entirety. Further materials that may be added include those disclosed in U.S. Pat. No. 4,830,028 to Lawson et al. and U.S. Pat. No. 8,186,360 to Marshall et al., the disclosures of which are incorporated herein by reference in their entireties.

In some implementations, the substrate material may comprise a liquid including an aerosol precursor composition and/or a gel including an aerosol precursor composition. Some examples of liquid compositions can be found in U.S. Pat. App. Pub. No. 2020/0113239 to Aller et al., which is incorporated herein by reference in its entirety.

As noted above, in various implementations, one or more of the substrate materials may have an aerosol precursor composition associated therewith. For example, in some implementations the aerosol precursor composition may comprise one or more different components, such as polyhydric alcohol (e.g., glycerin, propylene glycol, or a mixture thereof). Representative types of further aerosol precursor compositions are set forth in U.S. Pat. No. 4,793,365 to Sensabaugh, Jr. et al.; U.S. Pat. No. 5,101,839 to Jakob et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference. In some aspects, a substrate material may produce a visible aerosol upon the application of sufficient heat thereto (and cooling with air, if necessary), and the substrate material may produce an aerosol that is "smoke-like." In other aspects, the substrate material may produce an aerosol that is substantially non-visible but is recognized as present by other characteristics, such as flavor or texture. Thus, the nature of the produced aerosol may be variable depending upon the specific components of the aerosol delivery component. The substrate material may be chemically simple relative to the chemical nature of the smoke produced by burning tobacco.

In some implementations, the aerosol precursor composition may incorporate nicotine, which may be present in various concentrations. The source of nicotine may vary, and the nicotine incorporated in the aerosol precursor composition may derive from a single source or a combination of two or more sources. For example, in some implementations the aerosol precursor composition may include nicotine derived from tobacco. In other implementations, the aerosol precursor composition may include nicotine derived from other organic plant sources, such as, for example, non-tobacco plant sources including plants in the Solanaceae family. In other implementations, the aerosol precursor composition may include synthetic nicotine. In some implementations, nicotine incorporated in the aerosol precursor composition may be derived from non-tobacco plant sources, such as other members of the Solanaceae family. The aerosol precursor composition may additionally, or alternatively, include other active ingredients including, but not limited to, botanical ingredients (e.g., lavender, peppermint, chamomile, basil, rosemary, thyme, eucalyptus, ginger, cannabis, ginseng, maca, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C and cannabinoids, such as tetrahydrocannabinol (THC) and cannabidiol (CBD)). It should be noted that the aerosol precursor composition may comprise any constituents, derivatives, or combinations of any of the above.

As noted herein, the aerosol precursor composition may comprise or be derived from one or more botanicals or constituents, derivatives, or extracts thereof. As used herein, the term "botanical" includes any material derived from plants including, but not limited to, extracts, leaves, bark, fibres, stems, roots, seeds, flowers, fruits, pollen, husk, shells or the like. Alternatively, the material may comprise an active compound naturally existing in a botanical, obtained synthetically. The material may be in the form of liquid, gas, solid, powder, dust, crushed particles, granules, pellets, shreds, strips, sheets, or the like. Example botanicals are tobacco, eucalyptus, star anise, hemp, cocoa, cannabis, fennel, lemongrass, peppermint, spearmint, rooibos, chamomile, flax, ginger, *Ginkgo biloba*, hazel, hibiscus, laurel, licorice (liquorice), matcha, mate, orange skin, papaya, rose, sage, tea such as green tea or black tea, thyme, clove, cinnamon, coffee, aniseed (anise), basil, bay leaves, cardamom, coriander, cumin, nutmeg, oregano, paprika, rosemary, saffron, lavender, lemon peel, mint, juniper, elderflower, vanilla, wintergreen, beefsteak plant, curcuma, turmeric, sandalwood, cilantro, bergamot, orange blossom, myrtle, cassis, valerian, pimento, mace, damien, marjoram, olive, lemon balm, lemon basil, chive, carvi, verbena, tarragon, geranium, mulberry, ginseng, theanine, theacrine, maca, ashwagandha, damiana, guarana, chlorophyll, baobab or any combination thereof. The mint may be chosen from the following mint varieties: *Mentha* Arventis, *Mentha* c.v., *Mentha niliaca, Mentha piperita, Mentha piperita citrata* c.v., *Mentha piperita* c.v, *Mentha spicata crispa, Mentha cardifolia, Mentha longifolia, Mentha suaveolens variegata, Mentha pulegium, Mentha spicata* c.v. and *Mentha suaveolens.*

A wide variety of types of flavoring agents, or materials that alter the sensory or organoleptic character or nature of the mainstream aerosol of the smoking article may be suitable to be employed. In some implementations, such flavoring agents may be provided from sources other than tobacco and may be natural or artificial in nature. For example, some flavoring agents may be applied to, or incorporated within, the substrate material and/or those regions of the smoking article where an aerosol is generated. In some implementations, such agents may be supplied directly to a heating cavity or region proximate to the heat source or are provided with the substrate material. Example flavoring agents may include, for example, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, may also be suitable to be employed.

As used herein, the terms "flavor," "flavorant," "flavoring agents," etc. refer to materials which, where local regulations permit, may be used to create a desired taste, aroma, or other somatosensorial sensation in a product for adult consumers. They may include naturally occurring flavor materials, botanicals, extracts of botanicals, synthetically obtained materials, or combinations thereof (e.g., tobacco, cannabis, licorice (liquorice), hydrangea, eugenol, Japanese white bark magnolia leaf, chamomile, fenugreek, clove, maple, matcha, menthol, Japanese mint, aniseed (anise), cinnamon, turmeric, Indian spices, Asian spices, herb, wintergreen, cherry, berry, red berry, cranberry, peach, apple, orange, mango, clementine, lemon, lime, tropical fruit, papaya, rhubarb, grape, durian, dragon fruit, cucumber, blueberry, mulberry, citrus fruits, Drambuie, bourbon, scotch, whiskey, gin, tequila, rum, spearmint, peppermint, lavender, aloe vera, cardamom, celery, cascarilla, nutmeg, sandalwood, bergamot, geranium, khat, naswar, betel, shisha, pine, honey essence, rose oil, vanilla, lemon oil, orange oil, orange blossom, cherry blossom, cassia, caraway, cognac, jasmine, ylang-ylang, sage, fennel, wasabi, piment, ginger, coriander, coffee, hemp, a mint oil from any species of the genus *Mentha*, eucalyptus, star anise, cocoa, lemongrass, rooibos, flax, *Ginkgo biloba*, hazel, hibiscus, laurel, mate, orange skin, rose, tea such as green tea or black tea, thyme, juniper, elderflower, basil, bay leaves, cumin, oregano, paprika, rosemary, saffron, lemon peel, mint, beefsteak plant, curcuma, cilantro, myrtle, cassis, valerian, pimento, mace, damien, marjoram, olive, lemon balm, lemon basil, chive, carvi, verbena, tarragon, limonene, thymol, camphene), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, liquid such as an oil, solid such as a powder, or gas.

In some implementations, the flavor comprises menthol, spearmint and/or peppermint. In some embodiments, the flavor comprises flavor components of cucumber, blueberry, citrus fruits and/or redberry. In some embodiments, the flavor comprises eugenol. In some embodiments, the flavor comprises flavor components extracted from tobacco. In some embodiments, the flavor comprises flavor components extracted from cannabis.

In some implementations, the flavor may comprise a sensate, which is intended to achieve a somatosensorial sensation which are usually chemically induced and perceived by the stimulation of the fifth cranial nerve (trigeminal nerve), in addition to or in place of aroma or taste nerves, and these may include agents providing heating, cooling, tingling, numbing effect. A suitable heat effect agent may be, but is not limited to, vanillyl ethyl ether and a suitable cooling agent may be, but not limited to eucolyptol, WS-3.

Flavoring agents may also include acidic or basic characteristics (e.g., organic acids, such as levulinic acid, succinic acid, pyruvic acid, and benzoic acid). In some implementations, flavoring agents may be combinable with the elements of the substrate material if desired. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. Any of the materials, such as flavorings, casings, and the like that may be useful in combination with a tobacco material to affect sensory properties thereof, including organoleptic properties, such as described herein, may be combined with the substrate material. Organic acids particularly may be able to be incorporated into the substrate material to affect the flavor, sensation, or organoleptic properties of medicaments, such as nicotine, that may be able to be combined with the substrate material. For example, organic acids, such as levulinic acid, lactic acid, pyruvic acid, and benzoic acid may be included in the substrate material with nicotine in amounts up to being equimolar (based on total organic acid content) with the nicotine. Any combination of organic acids may be suitable. For example, in some implementations, the substrate material may include approximately 0.1 to about 0.5 moles of levulinic acid per one mole of nicotine, approximately 0.1 to about 0.5 moles of pyruvic acid per one mole of nicotine, approximately 0.1 to about 0.5 moles of lactic acid per one mole of nicotine, or combinations thereof, up to a concentration wherein the total amount of organic acid present is equimolar to the total amount of nicotine present in the substrate material. Various additional examples of organic acids employed to produce a substrate material are described in U.S. Pat. App. Pub. No. 2015/0344456 to Dull et al., which is incorporated herein by reference in its entirety.

The selection of such further components may be variable based upon factors such as the sensory characteristics that are desired for the smoking article, and the present disclosure is intended to encompass any such further components that are readily apparent to those skilled in the art of tobacco and tobacco-related or tobacco-derived products. See, Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties.

In other implementations, the substrate material may include other materials having a variety of inherent characteristics or properties. For example, the substrate material may include a plasticized material or regenerated cellulose in the form of rayon. As another example, viscose (commercially available as VISIL®), which is a regenerated cellulose product incorporating silica, may be suitable. Some carbon fibers may include at least 95 percent carbon or more. Similarly, natural cellulose fibers such as cotton may be suitable, and may be infused or otherwise treated with silica, carbon, or metallic particles to enhance flame-retardant properties and minimize off-gassing, particularly of any undesirable off-gassing components that would have a negative impact on flavor (and especially minimizing the likelihood of any toxic off-gassing products). Cotton may be treatable with, for example, boric acid or various organophosphate compounds to provide desirable flame-retardant properties by dipping, spraying or other techniques known in the art. These fibers may also be treatable (coated, infused, or both by, e.g., dipping, spraying, or vapor-deposition) with organic or metallic nanoparticles to confer the desired property of flame-retardancy without undesirable off-gassing or melting-type behavior.

In the depicted implementation, the substrate material 316 may comprise a centrally defined longitudinally extending axis between the opposed first and second ends, and a cross-section of the substrate material 316 may be, in some implementations, symmetrical about the axis. For example, in some implementations a cross-section of the substrate material may be substantially circular such that the substrate material defines a substantially cylindrical shape extending between the opposed first and second ends thereof. However, in other implementations, the substrate material may define a substantially non-circular cross-section such that the substrate material may define a substantially non-cylindrical shape between the opposed first and second ends thereof. Otherwise, in other examples, the substrate material may comprise an asymmetric cross-section about the axis. In various implementations, each end of the substrate material may be in axial alignment with adjacent elements.

In the depicted implementation, the outer housing comprises a rigid material. For example, the outer housing 312 of the depicted implementation is constructed of an aluminum material; however, in other implementations, the outer housing may be constructed of other materials, including other metal materials (such as, for example, stainless steel, aluminum, brass, copper, silver, gold, bronze, titanium, various alloys, etc.), or graphite materials, or ceramic materials, or plastic materials, or any combinations thereof. In some implementations, at least a portion of the heat source and/or at least a portion of the substrate material may be circumscribed by a paper foil laminate. In some implementations, the consumable unit may comprise an enclosure comprising a laminate that contains a heat source and a beaded substrate material. Some examples of laminates and/or enclosures that may be applicable to the present disclosure can be found in U.S. Pat. App. Pub. No. 2020/0128880 to Gage et al., which is incorporated herein by reference in its entirety.

In the depicted implementation, the outer housing 312 is constructed as a tube structure that substantially encapsulates the heat source 308 and the substrate material 316; however, as noted above, in other implementations the outer housing may have other shapes. Although the shape of the outer housing may vary, in the depicted implementation the outer housing 312 comprises a tube structure having opposed closed ends with openings defined therethrough. In particular, in addition to the heat source end openings 315, 317, the depicted implementation of the outer housing 312 also includes one or more end apertures 318 located on the opposite closed end that are configured to allow aerosolized vapor (herein alternatively referred to as a "vapor" or "aerosol") to pass therethrough. The end apertures 318 of the depicted implementation are in the form of a pair of elongate rounded slots; however, in other implementations the end apertures may have any form that permits passage of the aerosol therethrough. As such, it will be appreciated that the end apertures 318 can comprise fewer or additional apertures and/or alternative shapes and sizes of apertures than those illustrated.

The consumable unit of FIGS. 4 and 5 illustrate one implementation of a consumable unit configured for use with an inductive heating assembly, in accordance with the present disclosure. Other example implementations are shown in FIGS. 6-10. For example, FIG. 6 illustrates a schematic view of a removable consumable unit 400, according to another example implementation of the present disclosure. In the depicted implementation, the consumable unit 400 defines a first end 402 and a distal end 404. The consumable unit 400 of the depicted implementation further includes a heat portion 406 (which comprises a heat source 408), a substrate portion 410 (which comprises a substrate material 416), and a substrate container in the form of an outer housing 412 configured to circumscribe at least a portion of the heat source 408 and the substrate material 416.

In various implementations, the heat source may be configured to generate heat upon ignition thereof. In the depicted implementation, the heat source is a combustible fuel element. Reference is made to the discussion above regarding possible shapes, sizes, forms, compositions, construction methods, etc. of various heat sources. Generally, the heat source is positioned sufficiently near an aerosol delivery component (e.g., a substrate portion comprising a substrate material) having one or more aerosolizable components so that the aerosol formed/volatilized by the application of heat from the heat source to the aerosolizable components (as well as any flavorants, medicaments, and/or the like that are likewise provided for delivery to a user) is deliverable to the user by way of the mouthpiece. That is, when the heat source heats the substrate material, an aerosol is formed, released, or generated in a physical form suitable for inhalation by a consumer.

As shown in the figure, the substrate material 416 of the depicted implementation has opposed first and second ends, with the heat source 408 disposed adjacent the first end of the substrate material 416. In the depicted implementation, the substrate material 416 comprises tobacco beads, however, as noted above the substrate material of other implementations may differ. In the depicted implementation, the substrate portion 410 comprises a substrate material 416 having a single segment, although in other implementations the substrate portion may include one or more additional substrate material segments. As described above, in various implementations, one or more of the substrate materials may include a tobacco or tobacco related material, with an aerosol precursor composition associated therewith. In other implementations, non-tobacco materials may be used, such as a cellulose pulp material. In other implementations, the non-tobacco substrate material may not be a plant-derived material. Other possible compositions and/or components for use in a substrate material (and/or substrate materials) are described above. Reference is also made to the discussion above regarding various possible shapes, aerosol precursor compositions, additives, flavorants, etc. of the substrate material.

As shown in FIG. 6, the heat source 408 of the depicted implementation is contained within a susceptor pouch 420. In the depicted implementation, the outer housing 412 of the consumable unit 400 is configured to circumscribe the substrate portion 410 (which includes the substrate material 416), and a portion of the susceptor pouch 420. (Note that the outer housing is shown partially transparent in order to show the susceptor pouch 420.) In some implementations, the outer housing may circumscribe the entire susceptor pouch. In the depicted implementation, the outer housing comprises a tube structure and is made of a paper material (e.g., a paper tube having one or more layers). The depicted implementation of the outer housing 412 also includes one or more end apertures located on the first end of the outer housing 412 that are configured to allow aerosolized vapor (herein alternatively referred to as a "vapor" or "aerosol") to pass therethrough. As discussed above, the end apertures may have a variety of different shapes.

In the depicted implementation, the susceptor pouch 420 comprises a mesh structure 422 made of a susceptor material. In some implementations, the susceptor material may comprise a ferromagnetic material including, but not limited to, cobalt, iron, nickel, zinc, manganese, and any combinations thereof. In some implementations, the mesh structure made be made of other materials, including, for example, other metal materials such as aluminum or stainless steel, as well as ceramic materials such as silicon carbide. In still other implementations, the mesh structure may comprise other materials including metals such as copper, alloys of materials, or other materials with one or more susceptor materials imbedded therein. Various combinations of materials are also contemplated.

In some implementations, the mesh structure may comprise an interlaced structure of elongate components (e.g., wires or threads) that are crossed together and/or intersected so as to form a plurality of openings therebetween. In various implementations, the size (e.g., width and/or thickness) of the elongate components and/or the size of the openings created thereby may vary. In such a manner, the mesh pouch of various implementations of the present disclosure may confine the ignitable heat source 408 and provide openings that allow exposure to air thus aiding in the ignition of the heat source and continued combustion thereof. In some implementations, the susceptor pouch may comprise a flexible structure. In other implementations, the susceptor pouch may comprise a substantially rigid structure. In still other implementations, the susceptor pouch may comprise a combination of flexible and substantially rigid portions.

FIG. 7 illustrates a schematic view of a removable consumable unit 400, according to another example implementation of the present disclosure. In the depicted implementation, the consumable unit 500 defines a first end 502 and a distal end 504. The consumable unit 500 of the depicted implementation further includes a heat portion 506 (which comprises a heat source 508), a substrate portion 510 (which comprises a substrate material 516), and a substrate container in the form of an outer housing 512 configured to circumscribe at least a portion of the heat source 508 and the substrate material 516.

In various implementations, the heat source may be configured to generate heat upon ignition thereof. In the depicted implementation, the heat source is a combustible fuel element. Reference is made to the discussion above regarding possible shapes, sizes, forms, compositions, construction methods, etc. of various heat sources. Generally, the heat source is positioned sufficiently near an aerosol delivery component (e.g., a substrate portion comprising a substrate material) having one or more aerosolizable components so that the aerosol formed/volatilized by the application of heat from the heat source to the aerosolizable components (as well as any flavorants, medicaments, and/or the like that are likewise provided for delivery to a user) is deliverable to the user by way of the mouthpiece. That is, when the heat source heats the substrate material, an aerosol is formed, released, or generated in a physical form suitable for inhalation by a consumer.

As shown in the figure, the substrate material 516 of the depicted implementation has opposed first and second ends, with the heat source 508 disposed adjacent the first end of the substrate material 516. In the depicted implementation, the substrate material 516 comprises tobacco beads, however, as noted above the substrate material of other implementations may differ. In the depicted implementation, the substrate portion 510 comprises a substrate material 516 having a single segment, although in other implementations the substrate portion may include one or more additional substrate material segments. As described above, in various implementations, one or more of the substrate materials may include a tobacco or tobacco related material, with an aerosol precursor composition associated therewith. In other implementations, non-tobacco materials may be used, such as a cellulose pulp material. In other implementations, the non-tobacco substrate material may not be a plant-derived material. Other possible compositions and/or components for use in a substrate material (and/or substrate materials) are described above. Reference is also made to the discussion above regarding various possible shapes, aerosol precursor compositions, additives, flavorants, etc. of the substrate material.

As shown in FIG. 7, the heat source 508 of the depicted implementation is contained within a susceptor pouch 520. In the depicted implementation, the outer housing 512 of the consumable unit 500 is configured to circumscribe the substrate portion 510 (which includes the substrate material 516), and a portion of the susceptor pouch 520. (Note that the outer housing is shown partially transparent in order to show the susceptor pouch 520.) In some implementations, the outer housing may circumscribe the entire susceptor pouch.

In the depicted implementation, the susceptor pouch 520 comprises a mesh structure 522 made of a susceptor material. In some implementations, the susceptor material may comprise a ferromagnetic material including, but not limited to, cobalt, iron, nickel, zinc, manganese, and any combinations thereof. In some implementations, the mesh structure made be made of other materials, including, for example, other metal materials such as aluminum or stainless steel, as well as ceramic materials such as silicon carbide. In still other implementations, the mesh structure may comprise other materials including metals such as copper, alloys of materials, or other materials with one or more susceptor materials imbedded therein. Various combinations of materials are also contemplated.

In some implementations, the mesh structure may comprise an interlaced structure of elongate components (e.g., wires or threads) that are crossed together and/or intersected so as to form a plurality of openings therebetween. In various implementations, the size (e.g., width and/or thickness) of the elongate components and/or the size of the openings created thereby may vary. In such a manner, the mesh pouch of various implementations of the present disclosure may confine the ignitable heat source 408 and provide openings that allow exposure to air thus aiding in the ignition of the heat source and continued combustion thereof. In some implementations, the susceptor pouch may comprise a flexible structure. In other implementations, the susceptor pouch may comprise a substantially rigid structure. In still other implementations, the susceptor pouch may comprise a combination of flexible and substantially rigid portions.

In the depicted implementation, the outer housing 512 also comprises a mesh structure 522 made of a susceptor material. In some implementations, the susceptor material may comprise a ferromagnetic material including, but not limited to, cobalt, iron, nickel, zinc, manganese, and any combinations thereof. In some implementations, the mesh structure made be made of other materials, including, for example, other metal materials such as aluminum or stainless steel, as well as ceramic materials such as silicon carbide. In still other implementations, the mesh structure may comprise other materials including metals such as copper, alloys of materials, or other materials with one or more susceptor materials imbedded therein. Various combinations of materials are also contemplated. In some implementations, the susceptor pouch and the outer housing may be made of the same material or combination of materials. In other implementations, however, the susceptor pouch and the outer housing may be made of different materials or different combinations of materials.

In some implementations, the mesh structure of the outer housing (or a portion thereof) may comprise an interlaced structure of elongate components (e.g., wires or threads) that are crossed together and/or intersected so as to form a plurality of openings therebetween. In various implementations, the size (e.g., width and/or thickness) of the elongate components and/or the size of the openings created thereby may vary. In such a manner, openings proximate the first end of the outer housing 512 may be configured to allow aerosolized vapor to pass therethrough.

In some implementations, the heat source and the substrate material may together be contained in the susceptor pouch such that the susceptor pouch comprises the removable consumable unit. FIGS. 8-10 show example implementations of such a configuration. For example, FIG. 8 illustrates a schematic view of a removable consumable unit 600, according to another example implementation of the present disclosure. In the depicted implementation, the consumable unit 600 comprises a susceptor pouch 620 that includes a heat portion 606 (which comprises a heat source 608), and a substrate portion 610 (which comprises a substrate material 616).

In various implementations, the heat source may be configured to generate heat upon ignition thereof. In the depicted implementation, the heat source is a combustible fuel element. Reference is made to the discussion above regarding possible shapes, sizes, forms, compositions, construction methods, etc. of various heat sources. Generally, the heat source is positioned sufficiently near an aerosol delivery component (e.g., a substrate portion comprising a substrate material) having one or more aerosolizable components so that the aerosol formed/volatilized by the application of heat from the heat source to the aerosolizable components (as well as any flavorants, medicaments, and/or the like that are likewise provided for delivery to a user) is deliverable to the user by way of the mouthpiece. That is, when the heat source heats the substrate material, an aerosol is formed, released, or generated in a physical form suitable for inhalation by a consumer.

As shown in the figure, the substrate material 616 of the depicted implementation in located in one portion of the susceptor pouch 620 and is in contact with the heat source 608, which is located in another portion of the susceptor pouch 620. In the depicted implementation, the substrate portion 616 is located adjacent the heat source 608. In other implementations, however, other configurations are possible. In the depicted implementation, the substrate material 616 comprises tobacco beads, however, as noted above the substrate material of other implementations may differ. In the depicted implementation, the substrate portion 610 comprises a substrate material 616 having a single segment, although in other implementations the substrate portion may include one or more additional substrate material segments. As described above, in various implementations, one or more of the substrate materials may include a tobacco or tobacco related material, with an aerosol precursor composition associated therewith. In other implementations, non-tobacco materials may be used, such as a cellulose pulp material. In other implementations, the non-tobacco substrate material may not be a plant-derived material. Other possible compositions and/or components for use in a substrate material (and/or substrate materials) are described above. Reference is also made to the discussion above regarding various possible shapes, aerosol precursor compositions, additives, flavorants, etc. of the substrate material.

In the depicted implementation, the susceptor pouch 620 comprises a mesh structure 622 made of a susceptor material. In some implementations, the susceptor material may comprise a ferromagnetic material including, but not limited to, cobalt, iron, nickel, zinc, manganese, and any combinations thereof. In some implementations, the mesh structure made be made of other materials, including, for example, other metal materials such as aluminum or stainless steel, as well as ceramic materials such as silicon carbide. In still other implementations, the mesh structure may comprise other materials including metals such as copper, alloys of materials, or other materials with one or more susceptor materials imbedded therein. Various combinations of materials are also contemplated.

In some implementations, the mesh structure may comprise an interlaced structure of elongate components (e.g., wires or threads) that are crossed together and/or intersected so as to form a plurality of openings therebetween. In various implementations, the size (e.g., width and/or thickness) of the elongate components and/or the size of the openings created thereby may vary. In such a manner, the mesh pouch of various implementations of the present disclosure may confine the ignitable heat source 608 and substrate material 616 and provide openings that allow exposure to air thus aiding in the ignition of the heat source and continued combustion thereof. In some implementations, the susceptor pouch may comprise a flexible structure. In other implementations, the susceptor pouch may comprise a substantially rigid structure. In still other implementations, the susceptor pouch may comprise a combination of flexible and substantially rigid portions.

FIG. 9 illustrates a schematic cross-section view of a removable consumable unit 700, according to another example implementation of the present disclosure. In the depicted implementation, the consumable unit 700 comprises a susceptor pouch 720 that includes a heat portion 706 (which comprises a heat source 708), and a substrate portion 710 (which comprises a substrate material 716).

In various implementations, the heat source may be configured to generate heat upon ignition thereof. In the depicted implementation, the heat source is a combustible fuel element. Reference is made to the discussion above regarding possible shapes, sizes, forms, compositions, construction methods, etc. of various heat sources. Generally, the heat source is positioned sufficiently near an aerosol delivery component (e.g., a substrate portion comprising a substrate material) having one or more aerosolizable components so that the aerosol formed/volatilized by the application of heat from the heat source to the aerosolizable components (as well as any flavorants, medicaments, and/or the like that are likewise provided for delivery to a user) is deliverable to the user by way of the mouthpiece. That is, when the heat source heats the substrate material, an aerosol is formed, released, or generated in a physical form suitable for inhalation by a consumer.

As shown in the figure, the substrate material 716 of the depicted implementation is substantially surrounded by the heat source 708. In such a manner, the substrate portion 716 is located adjacent the heat source 708. In the depicted implementation, the substrate material 716 comprises tobacco beads, however, as noted above the substrate material of other implementations may differ. In the depicted implementation, the substrate portion 710 comprises a substrate material 716 having a single segment, although in other implementations the substrate portion may include one or more additional substrate material segments. As described above, in various implementations, one or more of the substrate materials may include a tobacco or tobacco related material, with an aerosol precursor composition associated therewith. In other implementations, non-tobacco materials may be used, such as a cellulose pulp material. In other implementations, the non-tobacco substrate material may not be a plant-derived material. Other possible compositions and/or components for use in a substrate material (and/or substrate materials) are described above. Reference is also made to the discussion above regarding various possible shapes, aerosol precursor compositions, additives, flavorants, etc. of the substrate material.

In the depicted implementation, the susceptor pouch 720 comprises a mesh structure 722 made of a susceptor material. In some implementations, the substrate material may be contained in a separate pouch within the susceptor pouch, and the separate pouch may also comprise a mesh structure made of a susceptor material, which may the same or different than the material of the susceptor pouch. In some implementations, the susceptor material may comprise a ferromagnetic material including, but not limited to, cobalt, iron, nickel, zinc, manganese, and any combinations thereof. In some implementations, the mesh structure made be made of other materials, including, for example, other metal materials such as aluminum or stainless steel, as well as ceramic materials such as silicon carbide. In still other implementations, the mesh structure may comprise other materials including metals such as copper, alloys of materials, or other materials with one or more susceptor materials imbedded therein. Various combinations of materials are also contemplated.

In some implementations, the mesh structure may comprise an interlaced structure of elongate components (e.g., wires or threads) that are crossed together and/or intersected so as to form a plurality of openings therebetween. In various implementations, the size (e.g., width and/or thickness) of the elongate components and/or the size of the openings created thereby may vary. In such a manner, the mesh pouch of various implementations of the present disclosure may confine the ignitable heat source 708 and substrate material 716 and provide openings that allow exposure to air thus aiding in the ignition of the heat source and continued combustion thereof. In some implementations, the susceptor pouch may comprise a flexible structure. In other implementations, the susceptor pouch may comprise a substantially rigid structure. In still other implementations, the susceptor pouch may comprise a combination of flexible and substantially rigid portions.

FIG. 10 illustrates a schematic cross-section view of a removable consumable unit 800, according to another example implementation of the present disclosure. In the depicted implementation, the consumable unit 800 comprises a susceptor pouch 820 that includes a heat portion 806 (which comprises a heat source 808), and a substrate portion 810 (which comprises a substrate material 816).

In various implementations, the heat source may be configured to generate heat upon ignition thereof. In the depicted implementation, the heat source is a combustible fuel element. Reference is made to the discussion above regarding possible shapes, sizes, forms, compositions, construction methods, etc. of various heat sources. Generally, the heat source is positioned sufficiently near an aerosol delivery component (e.g., the substrate portion) having one or more aerosolizable components so that the aerosol formed/volatilized by the application of heat from the heat source to the aerosolizable components (as well as any flavorants, medicaments, and/or the like that are likewise provided for delivery to a user) is deliverable to the user by way of the mouthpiece. That is, when the heat source heats the substrate material, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof. Additionally, the selection of various smoking article elements are appreciated upon consideration of commercially available electronic smoking articles, such as those representative products listed in the background art section of the present disclosure.

As shown in the figure, the heat source 808 of the depicted implementation is substantially surrounded by the substrate material 816. In such a manner, the substrate portion 816 is located adjacent the heat source 808. In the depicted implementation, the substrate material 816 comprises tobacco beads, however, as noted above the substrate material of other implementations may differ. In the depicted implementation, the substrate portion 810 comprises a substrate material 816 having a single segment, although in other implementations the substrate portion may include one or more additional substrate material segments. As described above, in various implementations, one or more of the substrate materials may include a tobacco or tobacco related material, with an aerosol precursor composition associated therewith. In other implementations, non-tobacco materials may be used, such as a cellulose pulp material. In other implementations, the non-tobacco substrate material may not be a plant-derived material. Other possible compositions and/or components for use in a substrate material (and/or substrate materials) are described above. Reference is also made to the discussion above regarding various possible shapes, aerosol precursor compositions, additives, flavorants, etc. of the substrate material.

In the depicted implementation, the susceptor pouch 820 comprises a mesh structure 822 made of a susceptor material. In some implementations, the heat source may be contained in a separate pouch within the susceptor pouch, and the separate pouch may also comprise a mesh structure made of a susceptor material, which may the same or different than the material of the susceptor pouch. In some implementations, the susceptor material may comprise a ferromagnetic material including, but not limited to, cobalt, iron, nickel, zinc, manganese, and any combinations thereof. In some implementations, the mesh structure made be made of other materials, including, for example, other metal materials such as aluminum or stainless steel, as well as ceramic materials such as silicon carbide. In still other implementations, the mesh structure may comprise other materials including metals such as copper, alloys of materials, or other materials with one or more susceptor materials imbedded therein. Various combinations of materials are also contemplated.

In some implementations, the mesh structure may comprise an interlaced structure of elongate components (e.g., wires or threads) that are crossed together and/or intersected so as to form a plurality of openings therebetween. In various implementations, the size (e.g., width and/or thickness) of the elongate components and/or the size of the openings created thereby may vary. In such a manner, the mesh pouch of various implementations of the present disclosure may confine the ignitable heat source 808 and substrate material 816 and provide openings (e.g., through the substrate material 816) that allow exposure to air thus aiding in the ignition of the heat source and continued combustion thereof. In some implementations, the susceptor pouch may comprise a flexible structure. In other implementations, the susceptor pouch may comprise a substantially rigid structure. In still other implementations, the susceptor pouch may comprise a combination of flexible and substantially rigid portions.

In various implementations, the present disclosure may also be directed to kits that provide a variety of components as described herein. For example, a kit may comprise a holder with one or more consumable units. In another implementation, a kit may comprise a main body with one or more mouthpiece portions. In another implementation, a kit may comprise a mouthpiece portion with one or more main bodies. In another implementation, a kit may comprise a plurality of holders. In further implementations, a kit may comprise a plurality of consumable units. In yet another implementation, a kit may comprise a plurality of holders and a plurality of consumable units. The inventive kits may further include a case (or other packaging, carrying, or storage component) that accommodates one or more of the further kit components. The case could be a reusable hard or soft container. Further, the case could be simply a box or other packaging structure. In some implementations, a brush or other cleanout accessory may be included in a kit. The cleanout accessory may be configured to be inserted in a receiving chamber of the holder, or, in other implementations, inserted in a separate aperture that enables a user to remove debris from the receiving chamber.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising:

a consumable unit comprising an ignitable heat source and a substrate material having an aerosol precursor composition configured to form an aerosol upon application of heat thereto; and a holder comprising a main body defining a proximal end and a distal end, the main body further defining a receiving chamber configured to receive the consumable unit and an aerosol passageway that extends through at least a portion of the main body, and an inductive heating assembly, wherein the heat source of the consumable unit is contained within and separate from a pouch that includes a susceptor material, wherein the inductive heating assembly is configured to heat the pouch that includes the susceptor material to ignite the ignitable heat source, wherein the pouch fully encloses the heat source, and wherein the consumable unit is removable and replaceable within the holder.

2. The aerosol delivery device of claim 1, wherein the substrate material is contained within a substrate container, and wherein at least a portion of the pouch that includes the susceptor material is in contact with the substrate material.

3. The aerosol delivery device of claim 2, wherein the substrate container comprises a substrate tube.

4. The aerosol delivery device of claim 3, wherein at least a portion of the substrate tube is constructed of a paper material.

5. The aerosol delivery device of claim 1, wherein the substrate material is also contained within the pouch that includes the susceptor material such that the pouch that includes the susceptor material comprises the consumable unit.

6. The aerosol delivery device of claim 1, wherein the inductive heating assembly includes a resonant transmitter comprising an inductor coil located proximate at least a portion of the receiving chamber.

7. The aerosol delivery device of claim 1, wherein the pouch that includes the susceptor material comprises a mesh structure.

8. The aerosol delivery device of claim 1, wherein the pouch that includes the susceptor material comprises a pouch that is made of the susceptor material.

9. The aerosol delivery device of claim 1, wherein the inductive heating assembly comprises a first portion configured to heat the pouch that includes the susceptor material, and a second portion configured to heat a portion of the substrate material.

10. The aerosol delivery device of claim 9, wherein the first and second portions are independently controllable.

11. A removable and replaceable consumable unit for use with a holder of an aerosol delivery device, the consumable unit comprising:

an ignitable heat source; and a substrate material having an aerosol precursor composition configured to form an aerosol upon application of heat thereto, wherein the heat source of the consumable unit is contained within and separate from a pouch that includes a susceptor material, wherein the pouch that includes the susceptor material is configured to be heated by an inductive heating assembly to ignite the heat source, and wherein the pouch fully encloses the heat source.

12. The removable and replaceable consumable unit of claim 11, wherein the substrate material is contained within a substrate container, and wherein at least a portion of the pouch that includes the susceptor material is in contact with the substrate material.

13. The removable and replaceable consumable unit of claim 12, wherein the substrate container comprises a substrate tube.

14. The removable and replaceable consumable unit of claim 13, wherein at least a portion of the substrate tube is constructed of a paper material.

15. The removable and replaceable consumable unit of claim 11, wherein the substrate material is also contained within the pouch that includes the susceptor material such that the pouch that includes the susceptor material comprises the consumable unit.

16. The removable and replaceable consumable unit of claim 11, wherein the pouch that includes the susceptor material is configured to be heated by an inductor coil.

17. The removable and replaceable consumable unit of claim 11, wherein the pouch that includes the susceptor material comprises a mesh structure.

18. The removable and replaceable consumable unit of claim 11, wherein the pouch that includes the susceptor material comprises a pouch that is made of susceptor material.

19. The removable and replaceable aerosol delivery device of claim 1, wherein the pouch that includes the susceptor material comprises a pouch that contains the susceptor material therewithin.

20. The removable and replaceable consumable unit of claim 11, wherein the pouch that includes the susceptor material comprises a pouch that contains the susceptor material therewithin.

* * * * *